United States Patent
Satoh et al.

(10) Patent No.: US 7,074,193 B2
(45) Date of Patent: Jul. 11, 2006

(54) PULSE WAVE ANALYSIS APPARATUS AND PULSE WAVE ANALYSIS PROGRAM PRODUCT FOR AUTOMATICALLY EXTRACTING CHARACTERISTIC POINTS OF PULSE WAVE

(75) Inventors: Hironori Satoh, Moriyama (JP); Takashi Inagaki, Kameoka (JP); Akira Oshiumi, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 11/149,441

(22) Filed: Jun. 10, 2005

(65) Prior Publication Data
US 2005/0283086 A1    Dec. 22, 2005

(30) Foreign Application Priority Data
Jun. 14, 2004    (JP) ............................. 2004-175958

(51) Int. Cl.
*A61B 5/00*    (2006.01)
(52) U.S. Cl. .................................................... 600/500
(58) Field of Classification Search ............ None
See application file for complete search history.

(56) References Cited

U.S. PATENT DOCUMENTS

| | | | |
|---|---|---|---|
| 6,616,613 B1 * | 9/2003 | Goodman | 600/504 |
| 2004/0210142 A1 * | 10/2004 | Satoh et al. | 600/485 |
| 2004/0210145 A1 * | 10/2004 | Satoh et al. | 600/500 |

FOREIGN PATENT DOCUMENTS

JP    07-039530    2/1995

* cited by examiner

*Primary Examiner*—Robert L. Nassar
(74) *Attorney, Agent, or Firm*—Morrison & Foerster LLP

(57) ABSTRACT

A pressure sensor for detecting a pulse wave, a digital conversion unit for converting a pressure signal from the pressure sensor into a digital signal, and a fourth derivative filter having an adjustable frequency characteristic for obtaining a fourth derivative wave of an original waveform based on the digital signal generated by the conversion by the digital conversion unit are provided. Local extrema of the fourth derivative wave in a section of the pulse wave corresponding to one beat are calculated. Based on the calculated local extrema, an early systolic component and a late systolic component are calculated.

22 Claims, 20 Drawing Sheets

PULSE WAVE ANALYSIS APPARATUS AND PULSE WAVE ANALYSIS PROGRAM PRODUCT FOR AUTOMATICALLY EXTRACTING CHARACTERISTIC POINTS OF PULSE WAVE

BACKGROUND OF THE INVENTION

1. Field of the Invention

The present invention relates to a pulse wave analysis apparatus and a pulse wave analysis program product and, in particular, to a pulse wave analysis apparatus and a pulse wave analysis program product for automatically extracting characteristic points of a pulse wave.

2. Description of the Background Art

Blood pressure is the pressure exerted against the internal walls of the arteries by blood flow generated by contraction and expansion of the heart, and consists of systolic pressure that is the blood pressure in a systolic phase of the heart and diastolic pressure that is the blood pressure in a diastolic phase of the heart. Pressure pulse wave of the intra-arterial pressure is a composite wave of an early systolic component (ejected wave) generated by ejection of blood from the heart and a late systolic component (reflected wave) generated by reflection mainly from the arteries.

Japanese Patent Laying-Open No. 07-039530 discloses an automatic sphygmomanometer that automatically analyzes the early systolic component and the late systolic component by determining a fourth derivative wave of the original waveform of a pulse wave.

The conventional automatic sphygmomanometer as disclosed in Japanese Patent Laying-Open No. 07-039530 uses a zero crossing point of the fourth derivative wave to determine the early systolic component and the late systolic component.

The zero crossing point used for determining the early systolic component and the late systolic component, however, is indefinite in some cases.

SUMMARY OF THE INVENTION

The present invention has been made in consideration of the aforementioned problem and, an object of the invention is to provide a pulse wave analysis apparatus and a pulse wave analysis program product that can stably calculate a characteristic point of a pulse wave.

According to an aspect of the present invention, a pulse wave analysis apparatus includes: a pressure sensor for detecting a pulse wave; a digital conversion unit for converting a pressure signal from the pressure sensor into a digital signal; a fourth derivative filter having an adjustable frequency characteristic for obtaining a fourth derivative wave of an original waveform based on the digital signal generated by the conversion by the digital conversion unit; a local extremum calculation unit for calculating local extrema of the fourth derivative wave in a section of the pulse wave corresponding to one beat; and a characteristic point calculation unit for calculating a characteristic point of the pulse wave.

The characteristic point calculation unit includes: a first calculation unit for calculating an early systolic component based on the local extrema of the fourth derivative wave; and a second calculation unit for calculating a late systolic component based on the local extrema of the fourth derivative wave.

Preferably, the first calculation unit includes a first characteristic point calculation unit for calculating a first characteristic point corresponding to a global maximum of the early systolic component by using a local maximum that is one of the local extrema of the fourth derivative wave and is located on an ascending limb from a pulse wave starting point to a pulse wave global-maximum point.

Preferably, the first calculation unit further includes a global maximum calculation unit for calculating the global maximum of the early systolic component based on a positional relation between the pulse wave starting point, the calculated first characteristic point and the pulse wave global-maximum point.

Preferably, the second calculation unit includes: a second characteristic point calculation unit for calculating a second characteristic point corresponding to a global maximum of the late systolic component by using a local maximum that is one of the local extrema of the fourth derivative wave and is located in a section of a descending limb from the pulse wave global-maximum point to a pulse-wave dicrotic notch point; an area calculation unit for calculating an area enclosed by a base and a portion of the fourth derivative wave from a first local minimum to a second local minimum, the first local minimum is one of the local extrema of the fourth derivative wave that is minimum in a section from the calculated first characteristic point to the calculated second characteristic point, the second local minimum is one of the local extrema of the fourth derivative wave that is minimum in a section from the second characteristic point to the pulse-wave dicrotic notch point, and the base is at larger one of the first local minimum and the second local minimum; a specific point calculation unit for calculating a specific point, on the fourth derivative wave, at which the area calculated by the area calculation unit is divided in a predetermined area ratio; and a global maximum calculation unit for calculating the global maximum of the late systolic component by using the specific point calculated by the specific point calculation unit.

Preferably, the first calculation unit further includes a rising point calculation unit for calculating a rising point of the early systolic component by using a local minimum that is one of the local extrema of the fourth derivative wave and is minimum in a section from the pulse wave starting point to the calculated first characteristic point.

Preferably, the second calculation unit includes: a second characteristic point calculation unit for calculating a second characteristic point corresponding to a global maximum of the late systolic component by using a local maximum that is one of the local extrema of the fourth derivative wave and is located in a section of a descending limb from the pulse wave global-maximum point to a pulse-wave dicrotic notch point; and a rising point calculation unit for calculating a rising point of the late systolic component by using a local minimum that is one of the local extrema of the fourth derivative wave and is minimum in a section from the calculated first characteristic point to the calculated second characteristic point.

Preferably, the second calculation unit includes a second characteristic point calculation unit for calculating a second characteristic point corresponding to a global maximum of the late systolic component by using a local maximum that is one of the local extrema of the fourth derivative wave and is located in a section of a descending limb from a pulse wave global-maximum point to a pulse-wave dicrotic notch point.

The pulse wave analysis apparatus preferably further includes a unit for calculating a ratio between an amplitude difference between a pulse wave starting point and a point on the pulse wave corresponding to a global maximum of the early systolic component calculated by the first calculation unit and an amplitude difference between the pulse wave starting point and a point on the pulse wave corresponding to a global maximum of the late systolic component calculated by the second calculation unit.

The pulse wave analysis apparatus preferably further includes a unit for calculating a ratio between an amplitude of a point on the fourth derivative wave used for calculating a global maximum of the early systolic component by the first calculation unit and an amplitude of a point on the fourth derivative wave used for calculating a global maximum of the late systolic component by the second calculation unit.

The pulse wave analysis apparatus preferably further includes a unit for calculating a time difference between a global maximum of the early systolic component calculated by the first calculation unit and a global maximum of the late systolic component calculated by the second calculation unit.

The pulse wave analysis apparatus preferably further includes a unit for calculating a time difference between a rising point of the early systolic component calculated by the first calculation unit and a rising point of the late systolic component calculated by the second calculation unit.

According to another aspect of the present invention, a pulse wave analysis program product is a pulse wave analysis program product for a computer to execute an analysis program of a pulse wave that is a composite wave of a first waveform and a second waveform. The analysis program includes: an obtaining step for obtaining a fourth derivative wave from the pulse wave corresponding to one beat; an extracting step for extracting local extrema of the obtained fourth derivative wave; a first calculation step for calculating the first waveform based on the extracted local extrema; and a second calculation step for calculating the second waveform based on the extracted local extrema.

Preferably, the first calculation step includes the step of calculating a first characteristic point corresponding to a global maximum of the first waveform by using a local maximum that is one of the extracted local extrema and is located on an ascending limb from a pulse wave starting point to a pulse wave global-maximum point.

Still preferably, the first calculation step further includes the step of calculating the global maximum of the first waveform based on a positional relation between the pulse wave starting point, the calculated first characteristic point and the pulse wave global-maximum point.

Still preferably, the second calculation step includes the steps of calculating a second characteristic point corresponding to a global maximum of the second waveform by using a local maximum that is one of the extracted local extrema and is located in a section of a descending limb from the pulse wave global-maximum point to a pulse-wave dicrotic notch point; calculating an area enclosed by a base and a portion of the fourth derivative wave from a first local minimum to a second local minimum, the first local minimum is one of the extracted local extrema that is minimum in a section from the calculated first characteristic point to the calculated second characteristic point, the second local minimum is one of the extracted local extrema that is minimum in a section from the second characteristic point to the pulse-wave dicrotic notch point, and the base is at larger one of the first local minimum and the second local minimum; calculating a specific point, on the fourth derivative wave, at which an area has a predetermined area ratio relative to the calculated area; and calculating the global maximum of the second waveform by using the calculated specific point.

Preferably, the first calculation step further includes the step of calculating a rising point of the first waveform by using a local minimum that is one of the extracted local extrema and is minimum in a section from the pulse wave starting point to the calculated first characteristic point.

Preferably, the second calculation step includes the steps of: calculating a second characteristic point corresponding to a global maximum of the second waveform by using a local maximum that is one of the extracted local extrema and is located in a section of a descending limb from the pulse wave global-maximum point to a pulse-wave dicrotic notch point; and calculating a rising point of the second waveform by using a local minimum that is one of the extracted local extrema and is minimum in a section from the calculated first characteristic point to the calculated second characteristic point.

The second calculation step preferably includes the step of calculating a second characteristic point corresponding to a global maximum of the second waveform by using a local maximum that is one of the extracted local extrema and is located in a section of a descending limb from a pulse wave global-maximum point to a pulse-wave dicrotic notch point.

Still preferably, the analysis program further includes the step of calculating a ratio between an amplitude difference between a pulse wave starting point and a point on the pulse wave corresponding to a global maximum of the first waveform calculated in the first calculation step and an amplitude difference between the pulse wave starting point and a point on the pulse wave corresponding to a global maximum of the second waveform calculated in the second calculation step.

Preferably, the analysis program further includes the step of calculating a ratio between an amplitude of a point on the fourth derivative wave used for calculating a global maximum of the first waveform in the first calculation step and an amplitude of a point on the fourth derivative wave used for calculating a global maximum of the second waveform in the second calculation step.

Preferably, the analysis program further includes the step of calculating a time difference between a global maximum of the first waveform calculated in the first calculation step and a global maximum of the second waveform calculated in the second calculation step.

Preferably, the analysis program further includes the step of calculating a time difference between a rising point of the first waveform calculated in the first calculation step and a rising point of the second waveform calculated in the second calculation step.

According to the present invention, the characteristic point of the pulse wave can stably be calculated. Moreover, the stable characteristic point can be used to automatically analyze the pulse wave.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
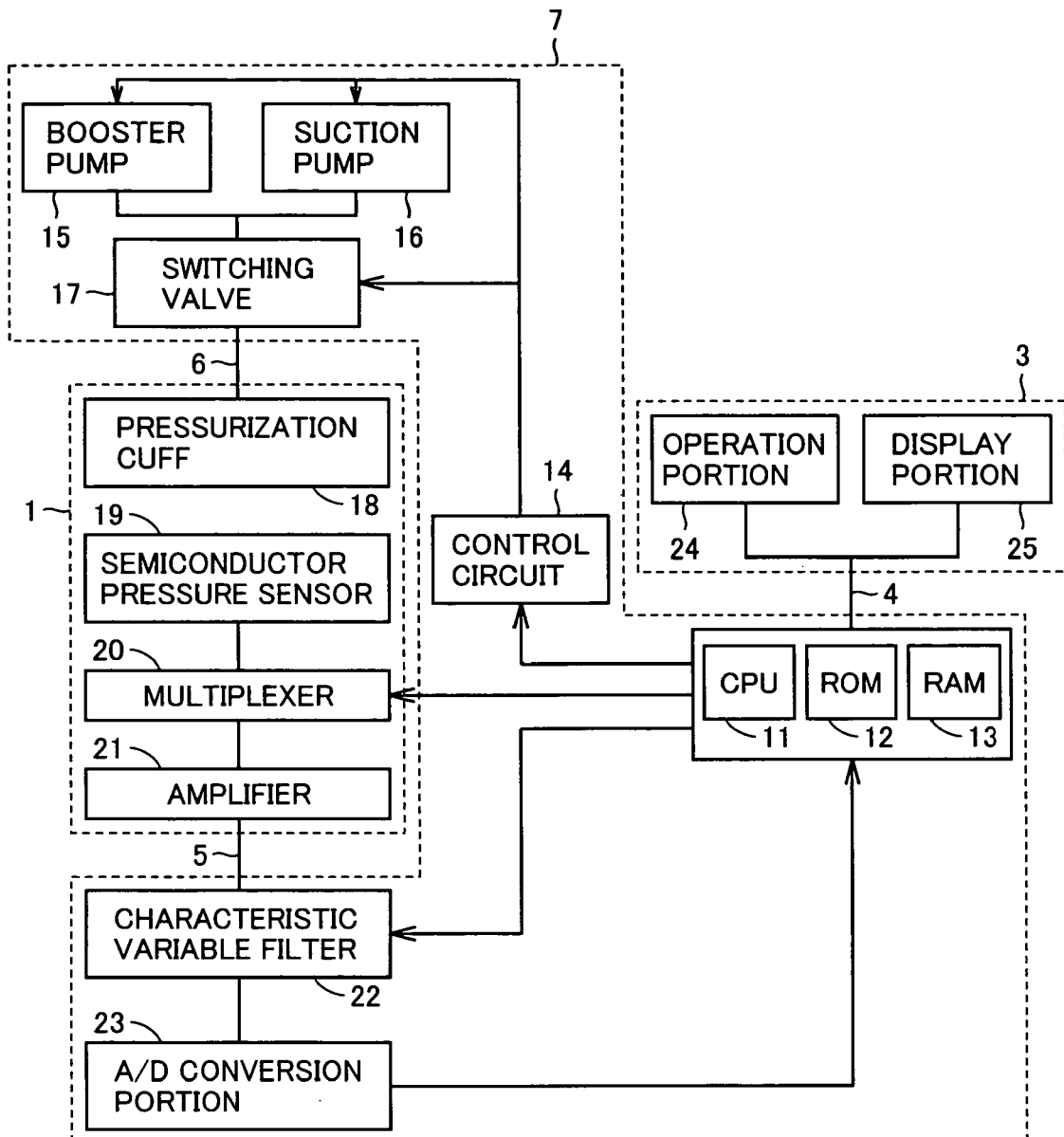
FIG. 1 shows a functional configuration of a pulse wave analysis apparatus according to a first embodiment of the present invention.

Embodiments of the present invention will hereinafter be described in detail with reference to the drawings. In the drawings, like components are denoted by like reference characters and a description thereof will not be repeated.

First Embodiment

FIG. 1 shows a functional configuration of a pulse wave analysis apparatus according to a first embodiment of the present invention. Referring to FIG. 1, a display unit 3 includes an operation portion 24 that is provided to be operable from the outside and is accordingly operated for entering various types of information including the one concerning a pulse wave analysis as well as a display portion 25 comprised of for example an LED (Light-Emitting Diode) and an LCD (Liquid Crystal Display) for outputting various types of information including the results of the pulse wave analysis.

A fixing base unit 7 includes a ROM (Read-Only Memory) 12 and a RAM (Random-Access Memory) 13 that store data and programs for controlling the pulse wave analysis apparatus, a CPU (Central Processing Unit) 11 performing various types of processing including an operation for concentrated control of the pulse wave analysis apparatus, a booster pump 15, a suction pump 16, a switching valve 17, a control circuit 14 receiving a signal from CPU 11 and transmitting the signal to booster pump 15, suction pump 16 and switching valve 17, a characteristic variable filter 22 that can be varied to at least two values, and an A/D conversion portion 23.

CPU 11 accesses ROM 12 to read a program and expand the program on RAM 13 for execution of the program to control the whole pulse wave analysis apparatus. CPU 11 receives from operation portion 24 an operation signal from a user and performs control processing for the whole pulse wave analysis apparatus based on the operation signal. Specifically, CPU 11 sends a control signal based on the operation signal that is input from operation portion 24. CPU 11 also displays the results of the pulse wave analysis for example on display portion 25.

Booster pump 15 is a pump for boosting the internal pressure (hereafter referred to as "cuff pressure") of a pressurization cuff (air bag) 18 described hereinlater, and suction pump 16 is a pump for decreasing the cuff pressure. Switching valve 17 selectively switches and connects one of booster pump 15 and suction pump 16 to an air tube 6. Control circuit 14 controls these components.

A sensor unit 1 includes a semiconductor pressure sensor 19 including a plurality of sensor elements, a multiplexer 20 selectively deriving a pressure signal output from each of these sensor elements, an amplifier 21 for amplifying the pressure signal output from multiplexer 20, and pressurization cuff 18 including the air bag having the pressure adjusted to press semiconductor pressure sensor 19 against a wrist.

Semiconductor pressure sensor 19 is configured to have a semiconductor chip made of single crystal silicon or the like that includes a plurality of sensor elements arranged on the chip in one direction at predetermined intervals, and is pressed, with the pressure of pressurization cuff 18, against a measurement site such as a wrist of a subject undergoing the measurement. In this state, semiconductor pressure sensor 19 detects a pulse wave of the subject via the radial artery. Semiconductor pressure sensor 19 inputs the pressure signal output upon the detection of the pulse wave to multiplexer 20 for each channel of the sensor element. The number of the arranged sensor elements is 40 for example.

Multiplexer 20 selectively outputs the pressure signal output from each sensor element. The pressure signal output from multiplexer 20 is amplified by amplifier 21 and selectively output to A/D conversion portion 23 via characteristic variable filter 22.

In this embodiment, until a sensor element that is most appropriate for the detection of the pulse wave is selected, multiplexer 20 is controlled by CPU 11 to output a plurality of pressure signals by turns that are output from respective sensor elements. After the sensor element that is most appropriate for the pulse wave detection is selected, CPU 11 fixes the relevant channel of the multiplexer. Multiplexer 20 accordingly selects and outputs the pressure signal output from the selected sensor element.

Characteristic variable filter 22 is a low-pass filter for cutting off signal components of a predetermined value or larger and can be changed to at least two values.

A/D conversion portion 23 converts the pressure signal, which is an analog signal derived from semiconductor pressure sensor 19, into digital information and provides the digital information to CPU 11. Until the channel of multiplexer 20 is fixed by CPU 11, A/D conversion portion 23 simultaneously receives pressure signals output from respective sensor elements included in semiconductor pressure sensor 19 via multiplexer 20. After CPU 11 fixes the channel of multiplexer 20, A/D conversion portion 23 receives the pressure signal that is output from the corresponding sensor element. The cycle period for sampling the pressure signal (hereinafter referred to as "sampling period") is for example 2 ms.

Characteristic variable filter 22 changes the cutoff frequency depending on whether it is before or after a channel of multiplexer 20 is fixed. Until the channel of multiplexer 20 is fixed, characteristic variable filter 22 samples a plurality of pressure signals by turns. Thus, a value of the cutoff frequency higher than the sampling frequency (20 kHz for example) at this time is selected. Lack of higher frequency information after the A/D conversion can thus be prevented and an optimum sensor element can appropriately be selected. After a channel is fixed, CPU 11 selects a value of the cutoff frequency that is half or below the sampling frequency (500 Hz for example) for a certain pressure signal. Accordingly, any aliasing noise can be reduced to precisely analyze the pulse wave. Here, the aliasing noise refers to noise, according to the sampling theorem, occurring when an analog signal is converted into a digital signal, with its frequency component at or higher than half the sampling frequency that appears in the region of frequencies at or lower than half the sampling frequency due to the aliasing phenomenon.

According to this embodiment, CPU 11, ROM 12 and RAM 13 are provided in fixing base unit 7 and thus display unit 3 can be reduced in size.

Although fixing base unit 7 and display unit 3 are provided here separately, respective functions of the units may be included in fixing base unit 7. In addition, although fixing base unit 7 includes CPU 11, ROM 12 and RAM 13, these components may be provided in display unit 3. Alternatively, they may be connected to a PC (personal computer) for various types of control to be performed.

Figure 2:
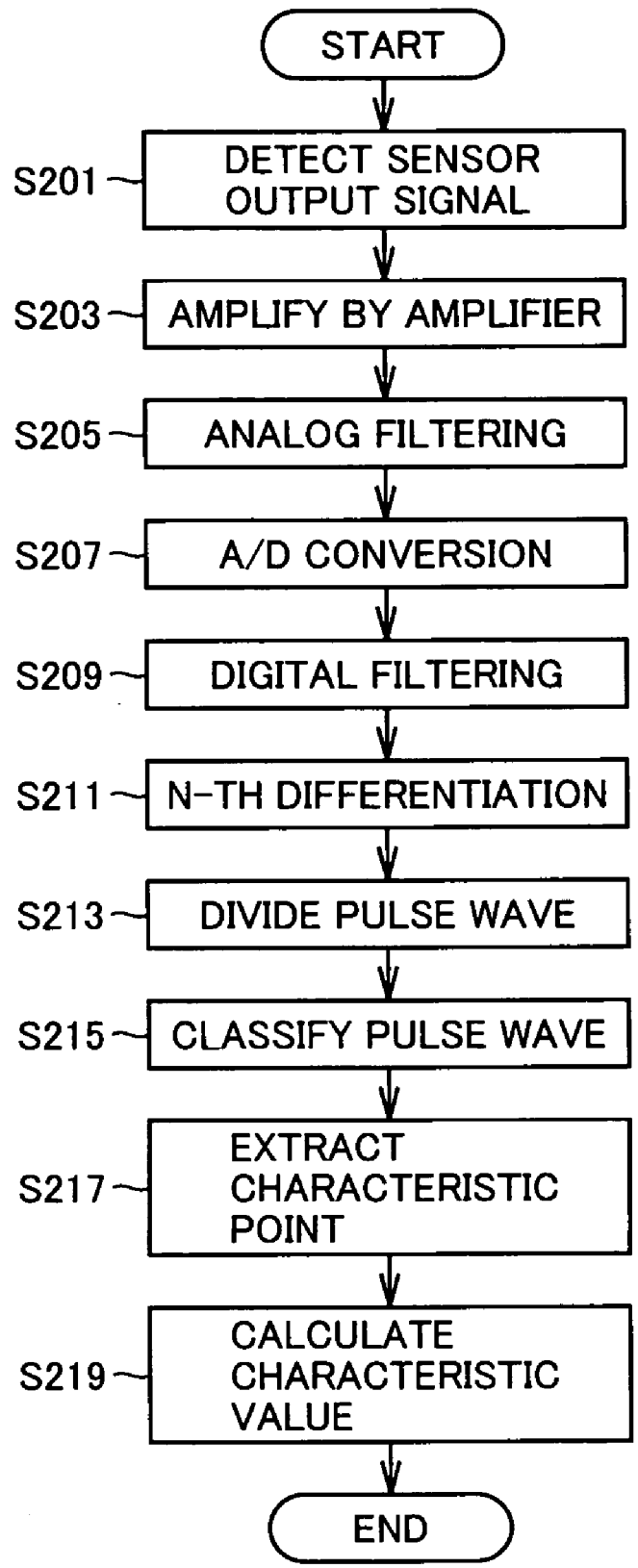
FIG. 2 is a flowchart showing a sensor signal analysis process according to the first embodiment of the present invention.

FIG. 2 is a flowchart showing a process of analyzing a pressure signal (sensor signal) from the sensor elements included in semiconductor pressure sensor 19 of the pulse wave analysis apparatus of the first embodiment. The process shown in the flowchart of FIG. 2 is implemented by CPU 11 in fixing base unit 7 that accesses ROM 12 for reading a program and expanding the program on RAM 13 to execute the program. Here, this process is described as a process of analysis after a channel of multiplexer 20 is fixed.

Referring to FIG. 2, firstly pressure signals are detected by semiconductor pressure sensor 19 having a plurality of sensor elements (S201) and then semiconductor pressure sensor 19 inputs the pressure signals to multiplexer 20. At this time, multiplexer 20 selects a sensor signal that is output from a sensor element corresponding to the designated channel. The pressure signal selected by multiplexer 20 is input to amplifier 21.

Amplifier 21 amplifies the pressure signal to a predetermined frequency (S203) and the pressure signal is analog-filtered by characteristic variable filter 22 (S205).

At this time, characteristic variable filter 22 cuts off signal components at and above half the sampling frequency. If the sampling frequency is 500 Hz, signal components of frequencies above 100 Hz for example are cut off.

The pressure signal passed through characteristic variable filter 22 is converted into a digital signal by A/D conversion portion 23 (S207) and digital-filtered for extracting frequencies in a predetermined range with the purpose for example of removing noise (S209). Then, A/D conversion portion 23 transfers the resultant digital pressure signal to CPU 11.

Then, receiving the pressure signal from A/D conversion portion 23, CPU 11 obtains first to fifth derivatives by differentiation of the data (S211). CPU 11 executes a program stored in ROM 12 to obtain an N-th derivative of a pulse waveform derived from the pressure signal.

Then, based on the result of the differentiation, the pulse waveform is divided to extract the pulse waveform of one beat (S213) and the pulse waveform is classified (S215). For example, the pulse waveform is classified depending on whether the waveform is a normal waveform or not and, if normal, the waveform is classified as any type.

From the classified pulse waveform, predetermined characteristic points are extracted (S217) to calculate a characteristic value that is for example AI (Augmentation Index) (S219). Then, the process of analyzing the sensor signal is completed.

The pulse wave analysis process in steps S213 to S219 is described in detail hereinlater.

The aforementioned AI is a well known index, which is an indexed version of the characteristic value reflecting the intensity of pulse wave reflection associated mainly with arteriosclerosis (a reflection phenomenon of the pulse wave, representing the susceptible blood stream). It is said that the AI is an effective index particularly for an early detection of circulatory disorder, and is known to exhibit a behavior different from that of the blood pressure.

The characteristic points of the pulse wave extracted in the aforementioned step S217 are described now.

For the analysis of the pulse wave, it is necessary to determine, for the characteristic points, an early systolic component (hereinafter referred to as "ejected wave") and a late systolic component (hereinafter referred to as "reflected wave").

Figure 3A:
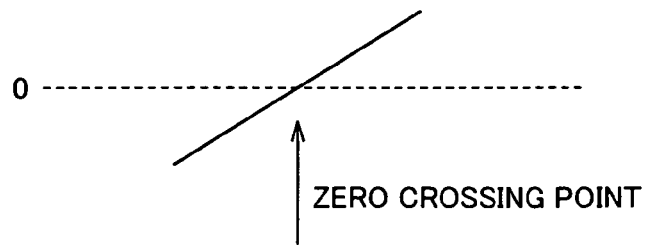
FIGS. 3A–3C show characteristics of zero crossing points.
Figure 3B:
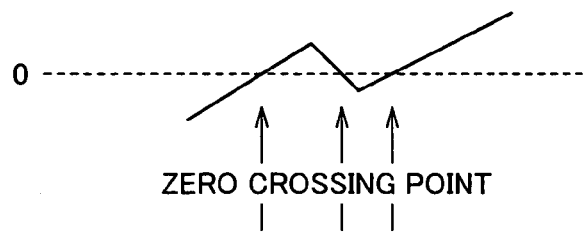
Figure 3C:
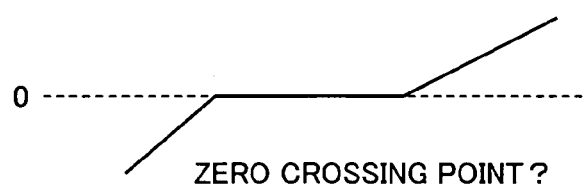

When characteristic points are to be extracted, zero crossing points of a fourth derivative wave obtained from an original waveform are generally used in most cases. Due to variations in base line for example, however, the zero crossing point extracted is not always a clear zero crossing point as shown in FIG. 3A. As shown in FIGS. 3B and 3C, the zero crossing point could be indefinite. In FIG. 3B, there are a plurality of zero crossing points and thus it is unclear which of the zero crossing points should be extracted as a characteristic point of the pulse waveform. In FIG. 3C, the value of zero is continuously detected for a certain period of time and thus the zero crossing point is indefinite.

If the zero crossing point is indefinite as shown in FIGS. 3B and 3C, there could arise the situation where a zero crossing point must be selected for extracting the characteristic point of the pulse wave.

Therefore, for an automatic analysis of the pulse wave, the zero crossing point used for extracting the characteristic point results in lack of stability. Stability is necessary for automatically analyzing the pulse wave. Then, for achieving the stability, such a point as local extremum that is not influenced by variations for example in base line may be used. Here, local extrema include a local maximum and a local minimum.

Since all signals are represented by Fourier series, a fourth derivative of a certain waveform is effective in extracting high-frequency components included in the waveform as explained below.

$$f(t) = \sin(t) + \sin(2t) \quad (1)$$

$$\frac{d}{dt}f(t) = \cos(t) + 2\cos(2t) \quad (2)$$

$$\frac{d^2}{dt^2}f(t) = -\sin(t) - 4\sin(2t)$$

$$\frac{d^3}{dt^3}f(t) = -\cos(t) - 8\cos(2t)$$

$$\frac{d^4}{dt^4}f(t) = \sin(t) + 16\sin(2t)$$

The term "sin(2t)" in expression (1) indicated above is represented by the fourth derivative as "16 sin(2t)" in expression (2). It is accordingly seen that the fourth derivative of a certain waveform is effective in extracting high-frequency components included in the waveform.

Figure 4:
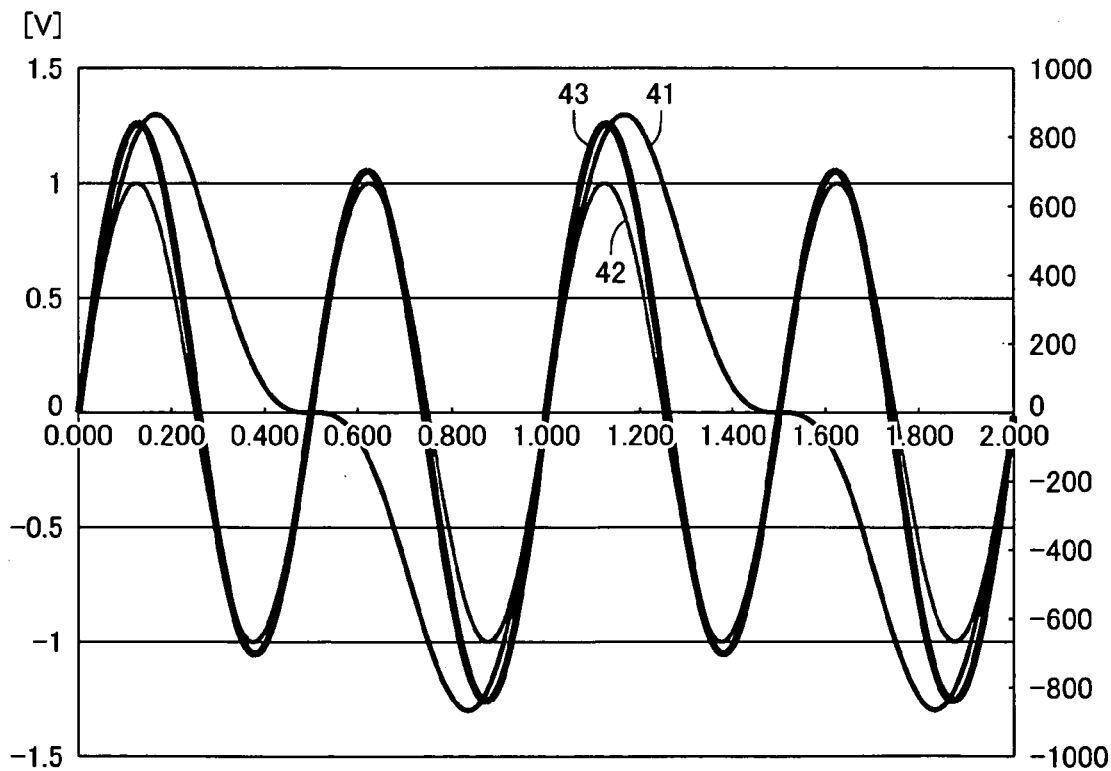
FIG. 4 shows an exemplary application of fourth derivative.

FIG. 4 shows an exemplary application of the fourth derivative. Referring to FIG. 4, a waveform 41 represents expression (1), a waveform 42 represents the term "sin(2t)" in expression (1) and a waveform 43 represents expression (2).

Waveform 43 is substantially identical in phase to waveform 42. Therefore, a local maximum of high frequency components included in the signal can be taken at a local maximum of the fourth derivative.

The ejected wave and the reflected wave have higher frequency compared with the cycle time of the pulse wave. Thus, local maxima of the fourth derivative of the pulse wave can be calculated to extract global maxima of the ejected wave and the reflected wave that are characteristic points.

As discussed above, the fourth derivative wave is susceptible to noise of high frequencies. Therefore, in some cases, it is difficult to extract the global maxima of the ejected wave and the reflected wave as characteristic points in the pulse wave analysis.

Expression (3) below is a differential expression of a discrete system.

$$f'(k) = \frac{f(k+1) - f(k-1)}{\Delta h} \quad (3)$$

In the differential expression as expression (3), the time interval (Δh) for differentiation (hereinafter referred to simply as "Δh") can be changed to adjust the maximum frequency included.

Figure 5:
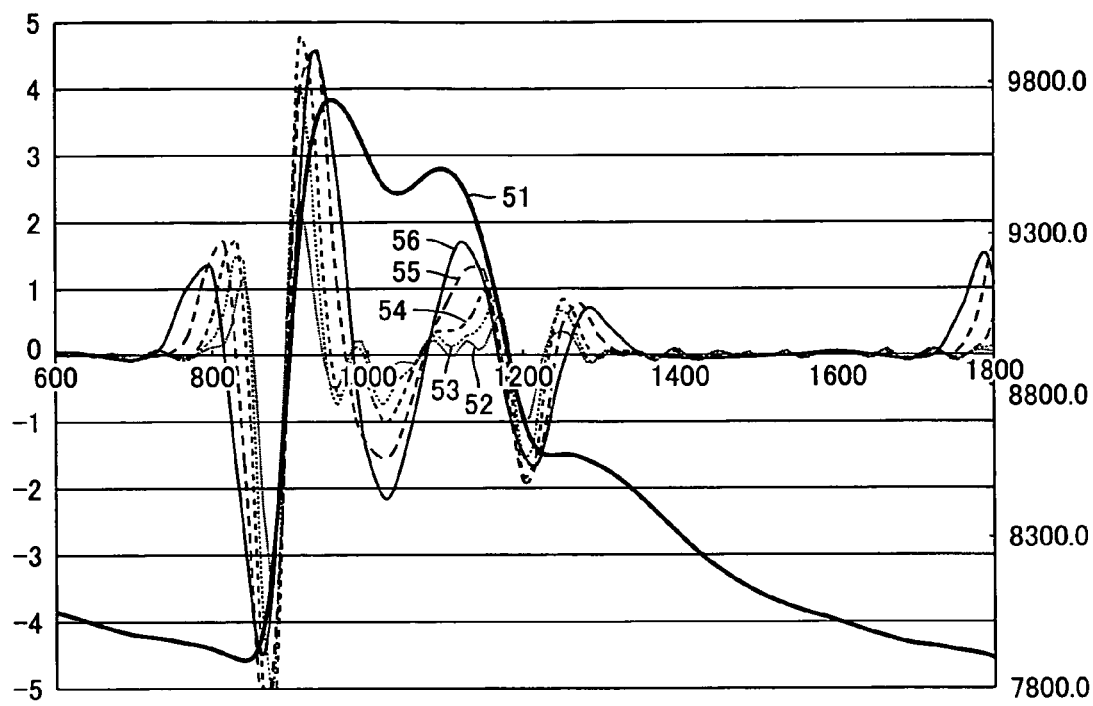
FIG. 5 illustrates frequency characteristics of a fourth derivative filter.

FIG. 5 shows examples with Δh of 8 ms, 12 ms, 16 ms, 24 ms and 32 ms respectively for an original waveform. In FIG. 5, a fourth derivative of original waveform 51 with Δh of 8 ms is represented by a waveform 52, the one with Δh of 12 ms is represented by a waveform 53, the one with Δh of 16 ms is represented by a waveform 54, the one with Δh of 24 ms is represented by a waveform 55, and the one with Δh of 32 ms is represented by a waveform 56.

Referring to FIG. 5, from a comparison between waveform 52 and waveform 56 for example, it is seen that waveform 52 shows faster changes and thus higher-frequency components are extracted. In contrast, waveform 56 shows slower changes and thus only the lower-frequency components are extracted. Thus, frequency characteristics of the fourth derivative filter can be adjusted to selectively extract a pulse-wave component.

An experiment was conducted through a simulation to see whether characteristic points of a pulse wave can successively be extracted by using local maxima of a fourth derivative wave obtained by means of such a fourth derivative filter.

Figure 6:
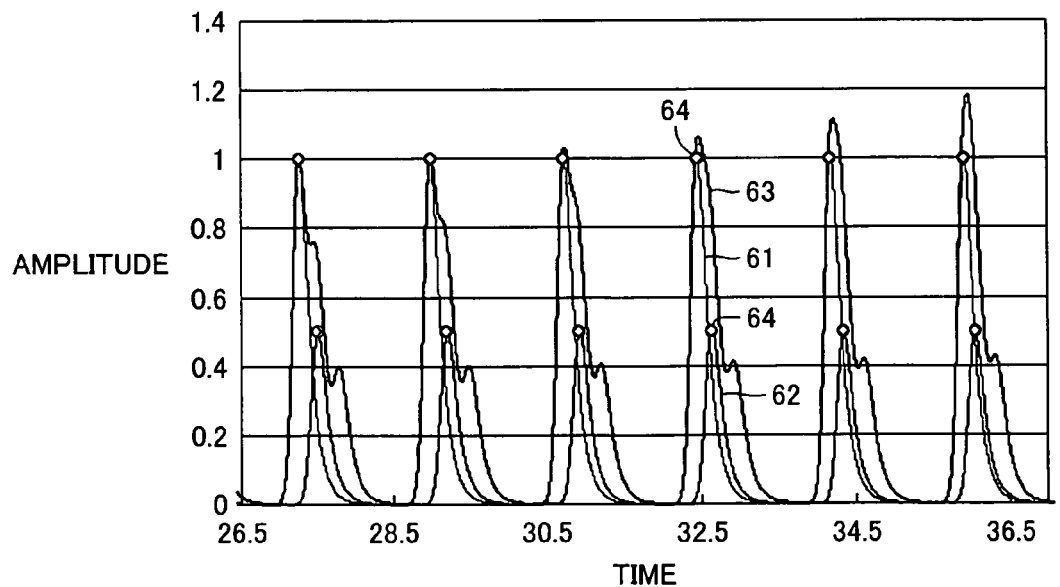
FIG. 6 shows an exemplary simulation for illustrating characteristics of local maxima of the fourth derivative.

FIG. 6 shows local maxima, found through the simulation, of a fourth derivative wave of a composite waveform of an ejected wave and a reflected wave.

Referring to FIG. 6, a waveform 63 represents a composite wave of an ejected wave 61 and a reflected wave 62 obtained through the simulation. It is seen that local maxima 64 obtained from the fourth derivative wave of composite wave 63 correspond to global maxima of ejected wave 61 and reflected wave 62.

In view of the above, the pulse wave analysis apparatus in the first embodiment uses local extrema of the fourth derivative wave obtained by the fourth derivative filter to extract characteristic points of the pulse wave. Since it is unnecessary to use a zero crossing point of the fourth derivative, the stability can be improved.

Further, the fourth derivative filter of the first embodiment has Δh longer than the sampling cycle period (2 ms) of data. Accordingly, noise included in high frequency components can be reduced. According to the present embodiment, Δh is for example 32 ms.

Figure 7:
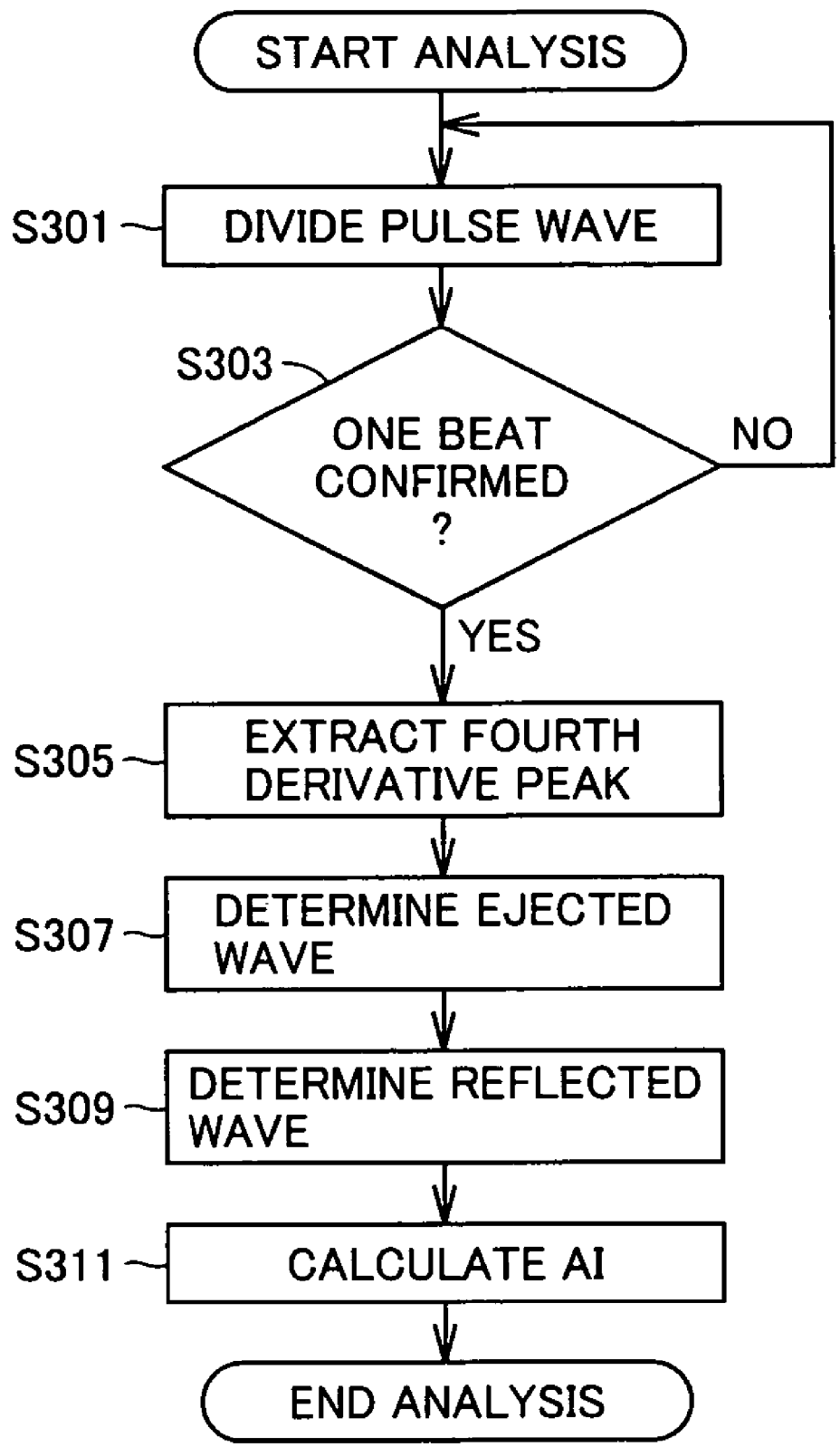
FIG. 7 is a flowchart showing a pulse wave analysis process according to the first embodiment of the present invention.
Figure 25:
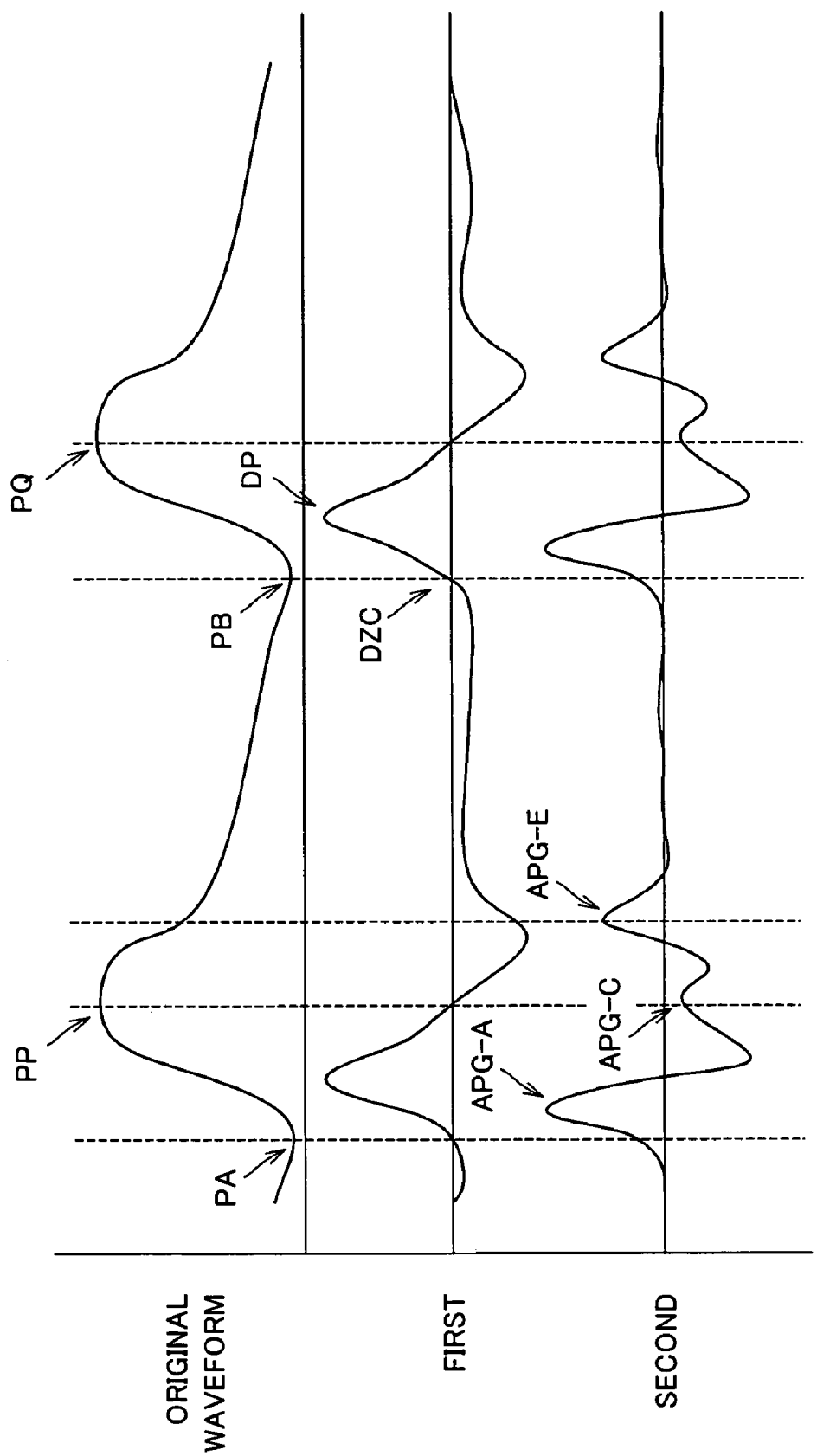
FIG. 25 partially shows FIG. 1 of Japanese Patent Laying-Open No. 07-039530 with reference characters added thereto.

The flowchart shown in FIG. 7 is used to describe, with reference to FIG. 25, the pulse wave analysis process in the first embodiment of the present invention. FIG. 25 shows a part of FIG. 1 of Japanese Patent Laying-Open No. 07-039530 to which reference characters are added.

Referring to FIG. 7, CPU 11 divides a pressure waveform that is continuously obtained to extract a pulse wave corresponding to one beat (S301). Specifically, referring to FIG. 25, a negative to positive transition of the first derivative among the N-th derivatives obtained in step S211 of FIG. 2 is waited for. When the first derivative changes from negative to positive, the rising zero crossing point (point DZC) is held and a point that is on the original waveform and in the same time phase as that of point DZC is defined as "temporary rising point (point PB)." Then a local maximum (point DP) of the first derivative is waited for.

When the local maximum (point DP) of the first derivative is detected, CPU 11 determines whether one beat can be confirmed or not (S303). Specifically, a local maximum (point PQ) of the original waveform is detected just after a temporary rising point (point PB). In response to the detection of the local maximum (point PQ), CPU 11 refers to the waveform from point PB to another temporary rising point (point PA) of a preceding beat. It is then confirmed that the global maximum (point PP) of the original waveform is present between point PA and point PB and point PB is the global minimum of the waveform between point PP and point PQ. Point PB is thus confirmed as the global minimum and accordingly point PB is defined as "rising point." The waveform from point PA to point PB is thus the pulse waveform of one beat. Point PA may also be defined as "pulse wave starting point."

The waveform of one beat is confirmed in S303 and then local maxima of the second derivative between point PA and point PB are obtained. The local maxima of the second derivative obtained here are referred to as point A (hereinafter "point APG-A"), point C (hereinafter "point APG-C") and point E (hereinafter "point APG-E") in order. Then, local maxima of the fourth derivative between point PA and point APG-E are obtained (S305). The obtained local maxima of the fourth derivative are candidates for the global maxima of the ejected wave and the reflected wave.

Among local maxima of the fourth derivative that are present in the section of the ascending limb between point PA and point PP, the maximum one is calculated as the global maximum (point P1) of the ejected wave (S307). Among local maxima of the fourth derivative that are present in the section of the descending limb between point PP and point APG-E, the maximum one is calculated as the global maximum (point P2) of the reflected wave (S309). It is noted that point PP could be the global maximum of the ejected wave or the global maximum of the reflected wave depending on cases. Accordingly, the aforementioned "section of the ascending limb" refers simply to the section from the pulse wave starting point (point PA) to the global maximum (point PP) of the pulse waveform. Further, the aforementioned "section of the descending limb" refers simply to the section from the global maximum (point PP) of the pulse waveform to the dicrotic notch point (point APG-E).

Point APG-E is used in an analysis as a point indicating the timing of closure of the aorta. Such a point on the pulse wave that indicates the timing of closure of the aorta is defined as "dicrotic notch point."

In the first embodiment, the global maximum of the fourth derivative wave in the section from point APG-A to point APG-C may be used to calculate the global maximum (P1) of the ejected wave. Further, the global maximum of the fourth derivative wave in the section from point APG-C to point APG-E may be used to calculate the global maximum (P2) of the reflected wave.

The global maxima of the ejected wave and the reflected wave are extracted in S307 and S309, and CPU 11 then calculates AI (S311). In the present embodiment, AI is the ratio, expressed as a percentage, of the amplitude difference between a point on the original waveform corresponding to point P2 and point PA relative to the amplitude difference between a point on the original waveform corresponding to point P1 and point PA.

Figure 8:
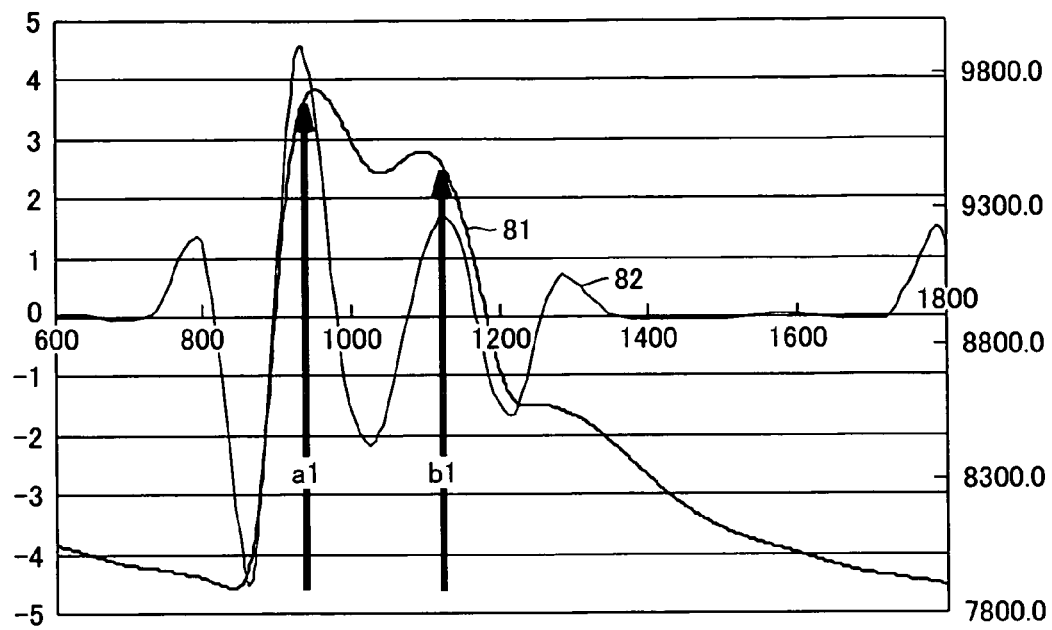
FIG. 8 shows a specific example of calculation of AI.

FIG. 8 shows AI in the present embodiment.

Referring to FIG. 8, a waveform 81 represents a pulse waveform and a waveform 82 represents a fourth derivative wave of waveform 81. An arrow a1 indicates the amplitude difference between the point on the original waveform corresponding to point P1 and point PA that is calculated in step S307. An arrow b1 indicates the amplitude difference between the point on the original waveform corresponding to point P2 and point PA that is calculated in step S309.

AI (%) is calculated as b1/a1×100. Regarding pulse waveform 81 shown in FIG. 8, the calculated AI is 80% (AI=80%).

Through the procedure described above, the pulse wave analysis process is completed.

As discussed above, in the present embodiment, the local maxima of the fourth derivative wave are determined for extracting the global maxima of the ejected wave and the reflected wave. In this case, the positional shift with respect to time is smaller than that of the case in which the zero crossing points of the fourth derivative wave are determined, and accordingly the stability can be improved.

Further, in the present embodiment, the fourth derivative filter having an appropriately selected time interval of the differentiation ($\Delta h$) is used and accordingly the pulse wave can automatically be analyzed for each beat.

Figure 9:
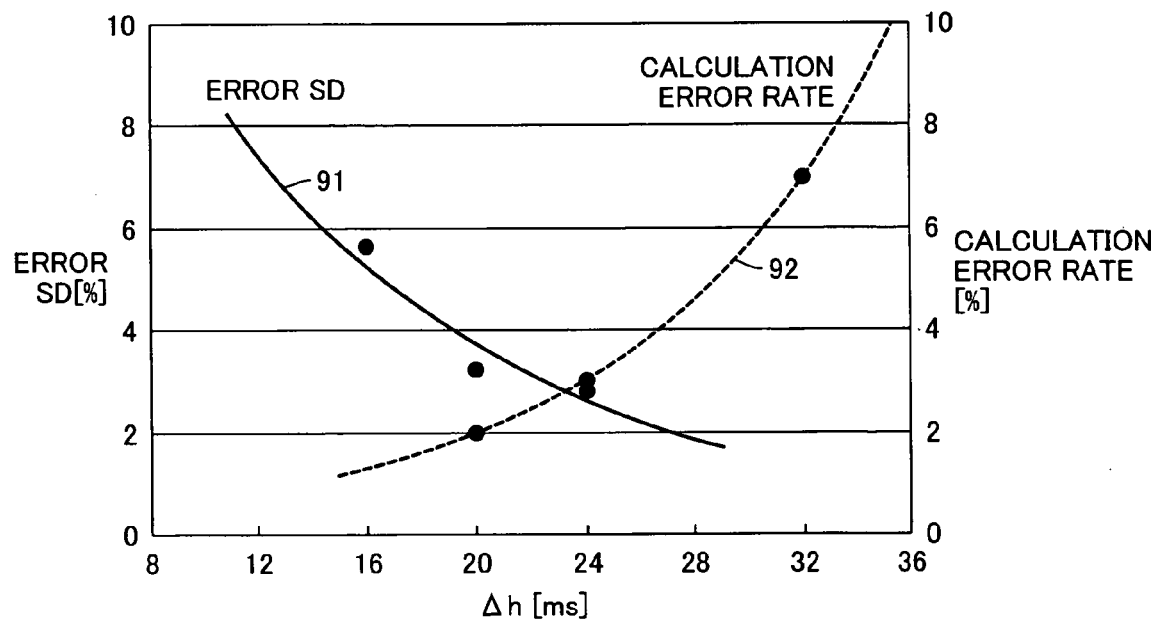
FIG. 9 shows performance of calculation of a characteristic value with respect to a difference in frequency characteristic of the fourth derivative filter.

Furthermore, according to the above-description of the present embodiment, although $\Delta h$ is 32 ms, $\Delta h$ is not limited to this one. For example, the graph as shown in FIG. 9 may be used to empirically determine an appropriate $\Delta h$.

In the present embodiment, since the sampling cycle period is 2 ms, $\Delta h$ is a multiple of 2 ms. Referring to FIG. 9, error SD (Standard Deviation) refers to standard deviation generated by changing $\Delta h$ for a group of waveforms with AI appropriately determined in advance. Calculation error rate refers to the rate of occurrences of events where a reflected wave component cannot be separated from a pulse waveform. Referring to a waveform 91 of the error SD, it is seen that as $\Delta h$ is larger, the error is smaller. Referring to a waveform 92 of the calculation error rate, it is seen that as $\Delta h$ is larger, the error rate is higher.

In view of the above, as $\Delta h$ that is stably determined by an algorism, 24 ms for example may be selected.

Second Embodiment

In a second embodiment of the present invention, a pulse wave analysis apparatus is similar in configuration and basic operation to that of the first embodiment.

Figure 26:
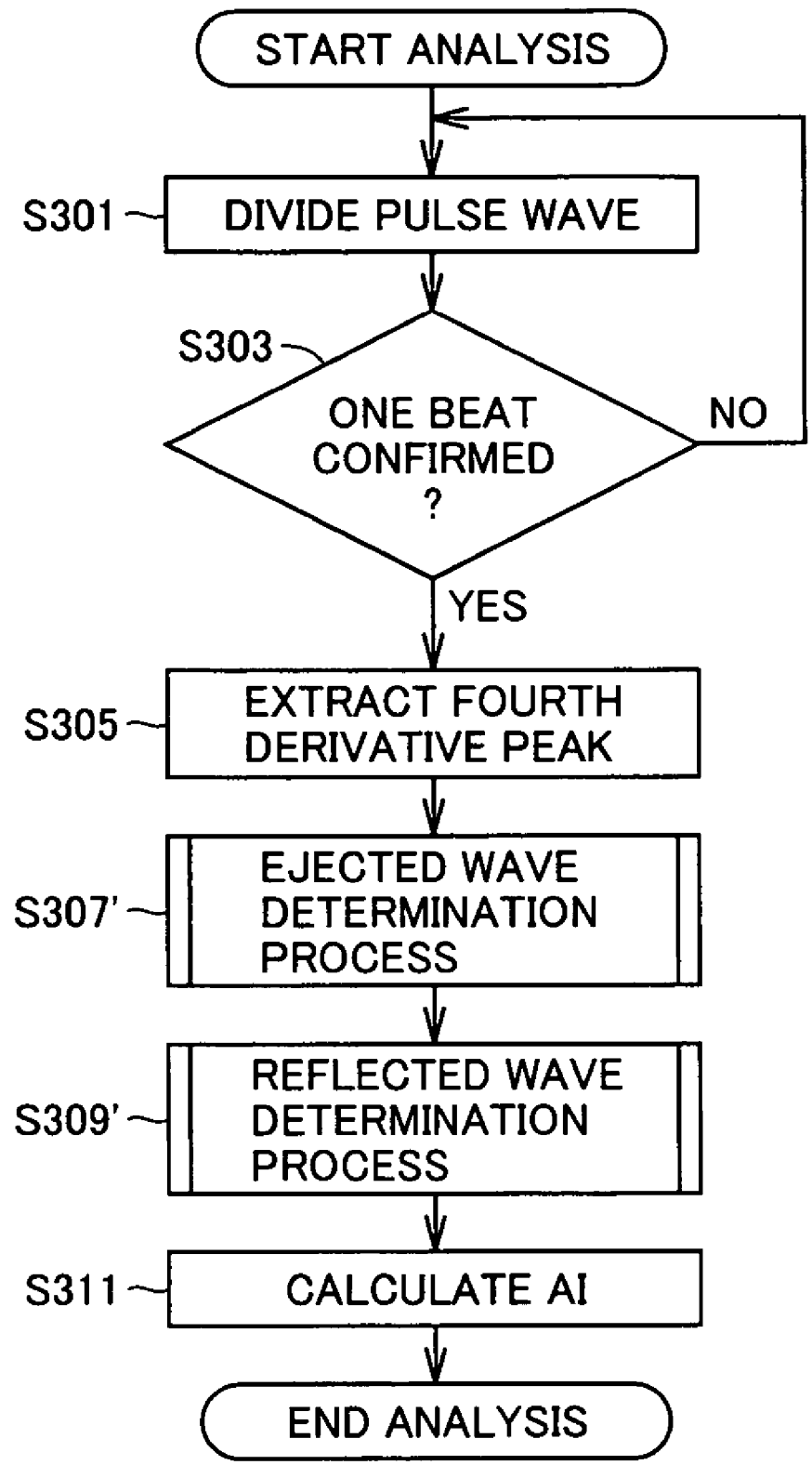
FIG. 26 is a flowchart showing a pulse wave analysis process according to a second embodiment of the present invention.

FIG. 26 is a flowchart showing a process of analyzing a pulse wave according to the second embodiment of the present invention. The pulse wave analysis process in the second embodiment differs from the one shown in the pulse wave analysis flowchart of FIG. 7, which is described in connection with the first embodiment, in the step of determining the ejected wave of step S307 and the step of determining the reflected wave of step S309. Here, the ejected wave determination step is indicated as step S307' and the reflected wave determination step is indicated as step S309' in FIG. 26. Other steps are common and the description thereof is not repeated here. Regarding step S307' and step S309', subroutines thereof are described hereinlater.

Regarding the first embodiment discussed above, it is supposed that the local maxima of the fourth derivative wave are identical in position to the global maxima of the ejected wave and the reflected wave. It is found, however, that they are not always identical to each other actually.

For confirmation, the following simulation is conducted.

Figure 10A:
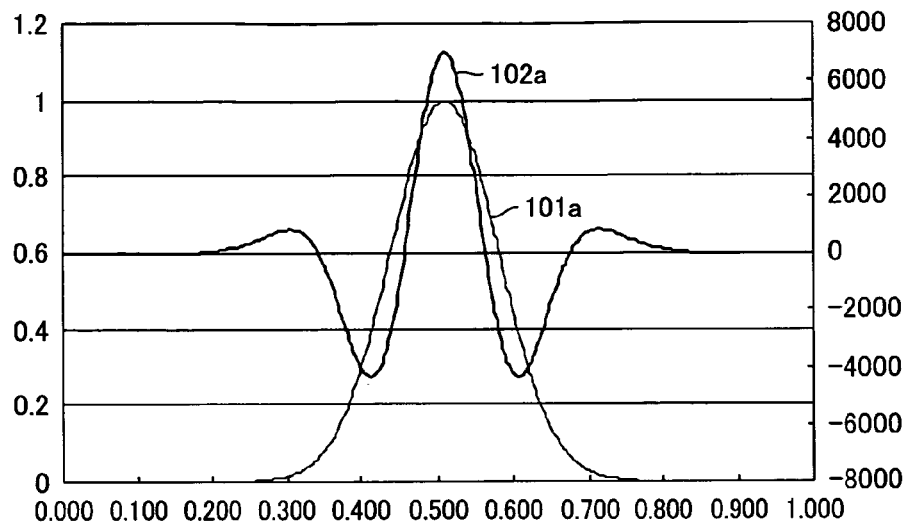
FIGS. 10A–10C show an exemplary simulation for illustrating a deviation between respective positions of local maxima of an original waveform and a fourth derivative wave.
Figure 10B:
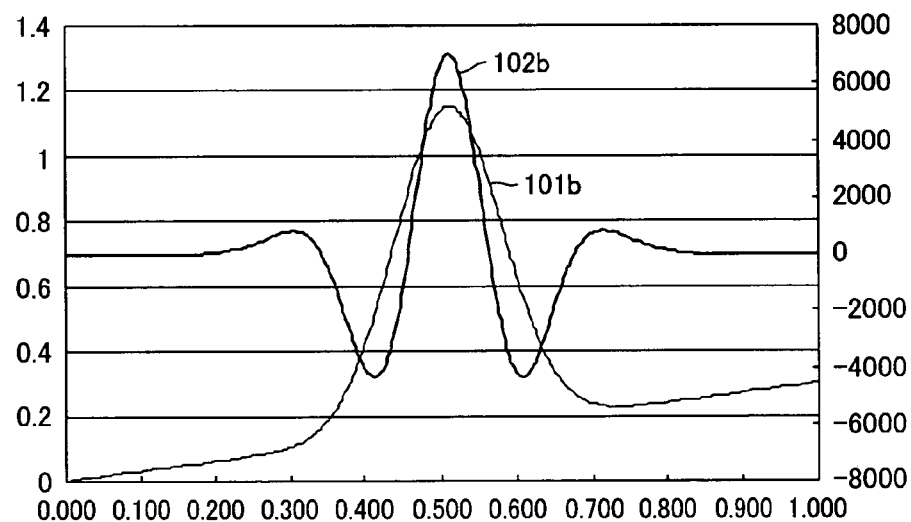
Figure 10C:
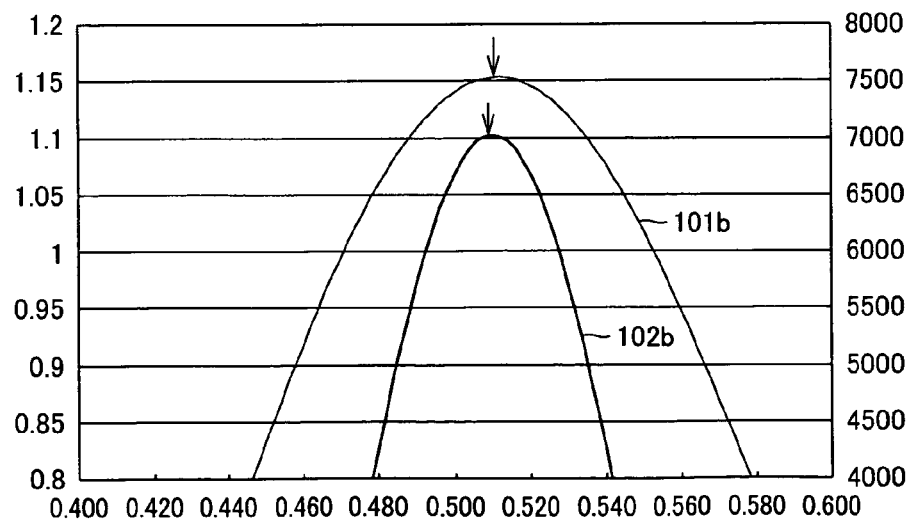

FIGS. 10A to 10C show an example of a fourth derivative of a Gaussian function in the simulation.

Referring to FIG. 10A, the fourth derivative of the Gaussian function (waveform 101a) provides the fourth derivative wave indicated as a waveform 102a. In this case, the position of the local maximum of waveform 101a of the Gaussian function and that of waveform 102a of the fourth derivative wave match each other.

Then, the base line of the Gaussian function as indicated by waveform 101a in FIG. 10A is varied. In this simulation, the variation of the base line is implemented by a linear function with respect to time.

Consequently, as shown in FIG. 10B, while a waveform 101b of the Gaussian function tilts, a waveform 102b of the fourth derivative wave thereof does not tilt. In this case, as shown in FIG. 10C, respective positions of the local maximum of waveform 101b and that of waveform 102b deviate from each other.

Since the variation of the base line is implemented by the linear function in the simulation as described above, information about the variation of the base line is lost by the derivative of the first time. In this case, the peak position of the original waveform is changed due to the influence of a term that does not appear in the fourth derivative. It is accordingly found that the peak position of the original waveform cannot be obtained in some cases by the fourth derivative.

Through the simulation, it is found that the global maxima of the ejected wave and the reflected wave should be determined based on local maxima of the fourth derivative wave with some corrections.

Determination of Ejected Wave

When the pulse wave is analyzed, the global maximum of the pulse wave matches the global maximum of the ejected wave in some cases and they do not match in other cases. When they do not match, a descending component of the ejected wave and an ascending component of the reflected wave are superimposed on each other to form the global maximum of the pulse wave. In this case, any local maximum of the fourth derivative does not match the global maximum of the pulse wave and accordingly the global maximum of the ejected wave can be determined.

However, as seen from the result of the simulation described in connection with FIGS. 10A to 10C, the global maximum of the pulse wave does not necessarily match the global maximum of the ejected wave even if there is no superimposition of the reflected wave. For example, when the base line is varied for example to cause a loss of the partial symmetry with respect to the global maximum of the pulse wave, the position of the local maxima of the fourth derivative shifts.

Thus, in the present embodiment, CPU 11 uses an ejected wave correction algorithm as discussed below to determine the global maximum of the ejected wave.

Figure 11:
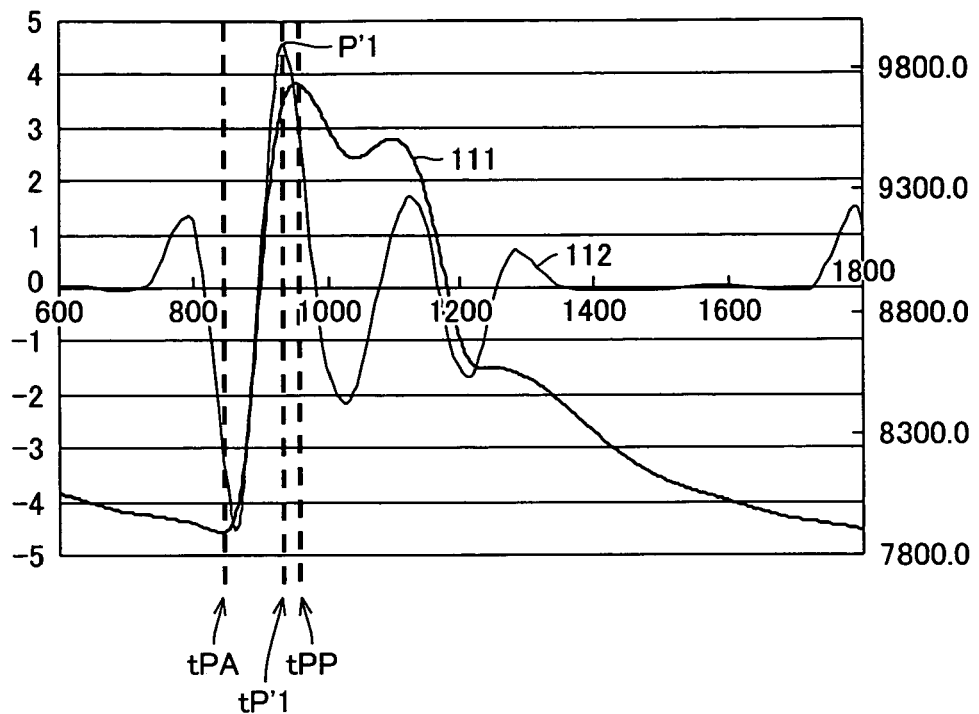
FIG. 11 illustrates an ejected wave correction algorithm.
Figure 27:
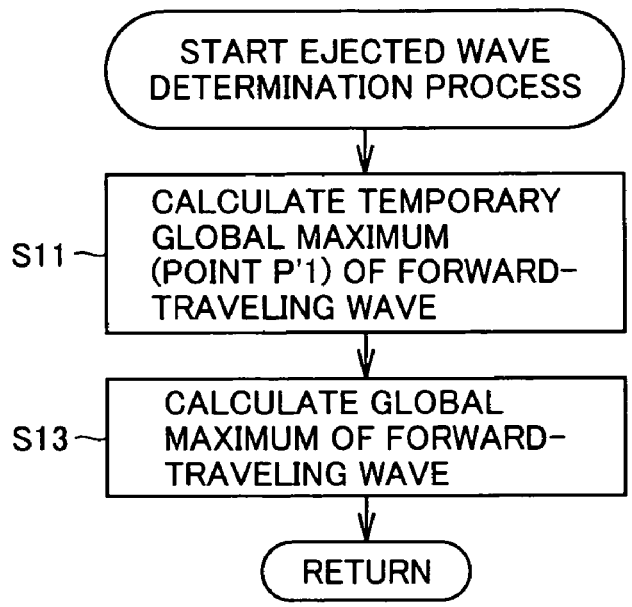
FIG. 27 is a flowchart showing a flow of an ejected wave determination process in step S307' of FIG. 26.

FIG. 27 is a flowchart showing a flow of the process of determining the ejected wave in step S307' of FIG. 26. In the first embodiment, the local maximum of the fourth derivative wave that is present in the section of the ascending limb is used to calculate the global maximum of the ejected wave. In the second embodiment, based on the local maximum of the fourth derivative wave, the correction as indicated in step S13 is made. FIG. 11 illustrates the ejected wave correction algorithm.

Referring to FIG. 27, a temporary global maximum of the ejected wave (hereinafter referred to as "point P'1") is calculated (step S11).

Here, with reference to FIG. 11, a waveform 111 represents a pulse wave and a waveform 112 represents a fourth derivative wave of pulse wave 111. Point P'1 is the local maximum of fourth derivative wave 112 by which the global maximum of the ejected wave is determined in the first embodiment. The global maximum of the ejected wave (point P1) is determined from the positional relation between the global maximum of pulse wave 111 (point PP), point P'1 and the rising point of pulse wave 111 (point PA).

CPU 11 uses a predetermined expression for calculating the global maximum of the ejected wave (point P1) (step S13). Specifically, the expression indicated below is used for the calculation. Respective times (values on the time axis) of point PP, point P'1, point PA and point P1 are represented as tPP, tP'1, tPA and tP1. Further, correction coefficients $\alpha_1$ and $\beta$ as well as a correction parameter $\gamma$ are used.

In this case, tP1 is determined by expression (4) below.

$$\gamma = \alpha_1 \times (tP'1 - tPA)/(tPP - tPA) + \beta; tP1 = \gamma \times (tPP - tP'1) + tP'1 \quad (4)$$

Here, the condition $\gamma < 0$ is regarded as $\gamma = 0$ and the condition $\gamma > 1$ is regarded as $\gamma = 1$.

A point on fourth derivative wave 112 that is at the position of tP1 is confirmed as point P1.

In the present embodiment, correction coefficients $\alpha_1$ and $\beta$ are determined from a comparison between the simulation and the conventional algorithm. The correction coefficients thus determined are for example $\alpha_1 = 1.5$ and $\beta = 0.3$.

Determination of Reflected Wave

The ejected wave is the wave of blood ejected from the heart while the reflected wave is the wave reflected from various points to be transmitted. The waves are superimposed on each other to be integrated into a seemingly large wave. However, an analysis of the wave by the fourth derivative may find a plurality of waves in some cases. Further, even if the wave seems to be a single wave, the wave is actually a plurality of components superimposed on each other and thus the center of gravity of the wave does not always match a local maximum of a fourth derivative wave.

Then, in the present embodiment, CPU 11 uses the following reflected-wave correction algorithm to determine the reflected wave.

Figure 12:
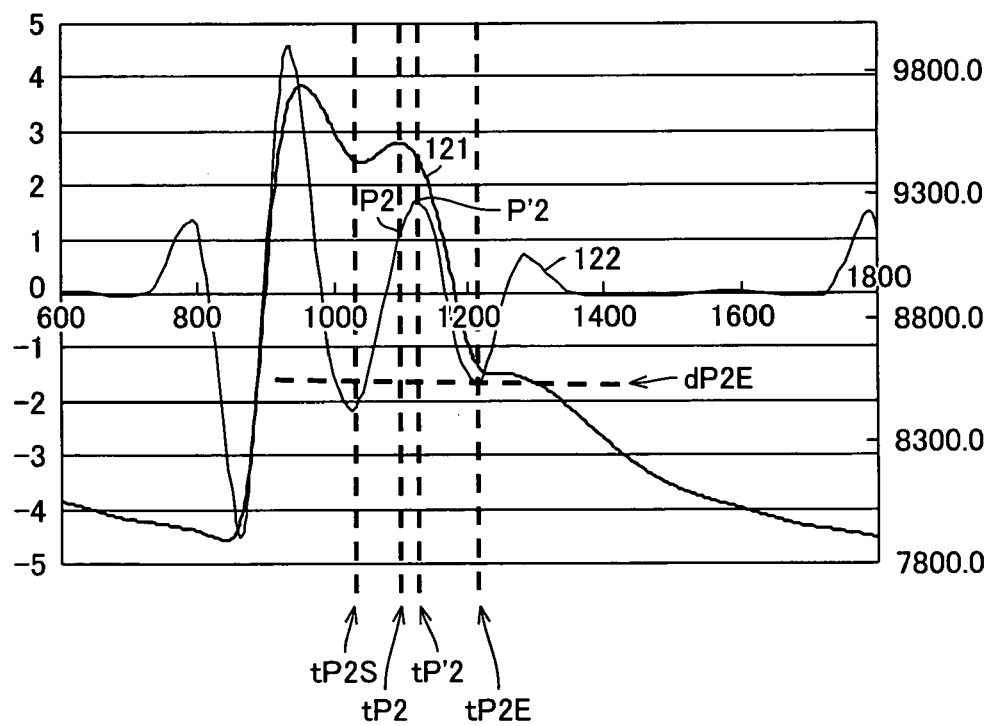
FIG. 12 illustrates a reflected wave correction algorithm.
Figure 13:
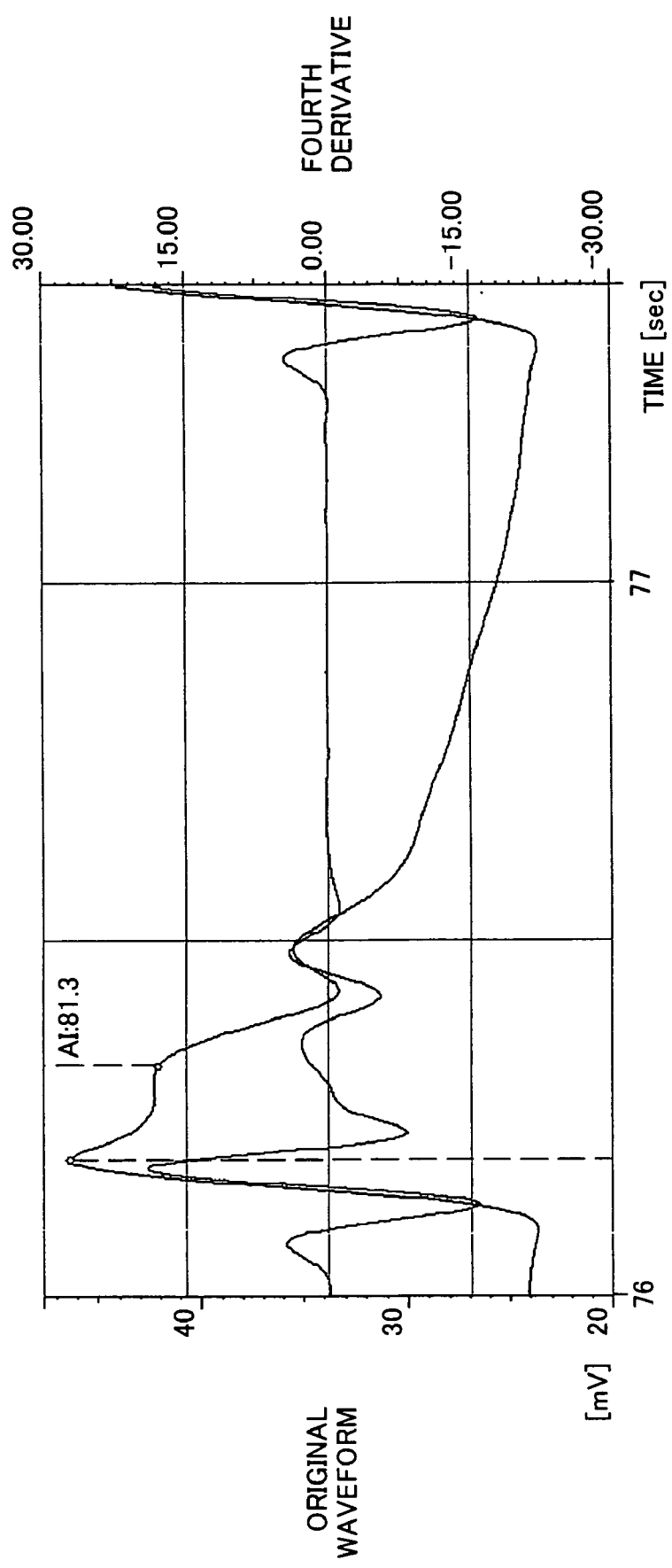
FIGS. 13–16 each show an exemplary pulse wave analysis of a living body.
Figure 14:
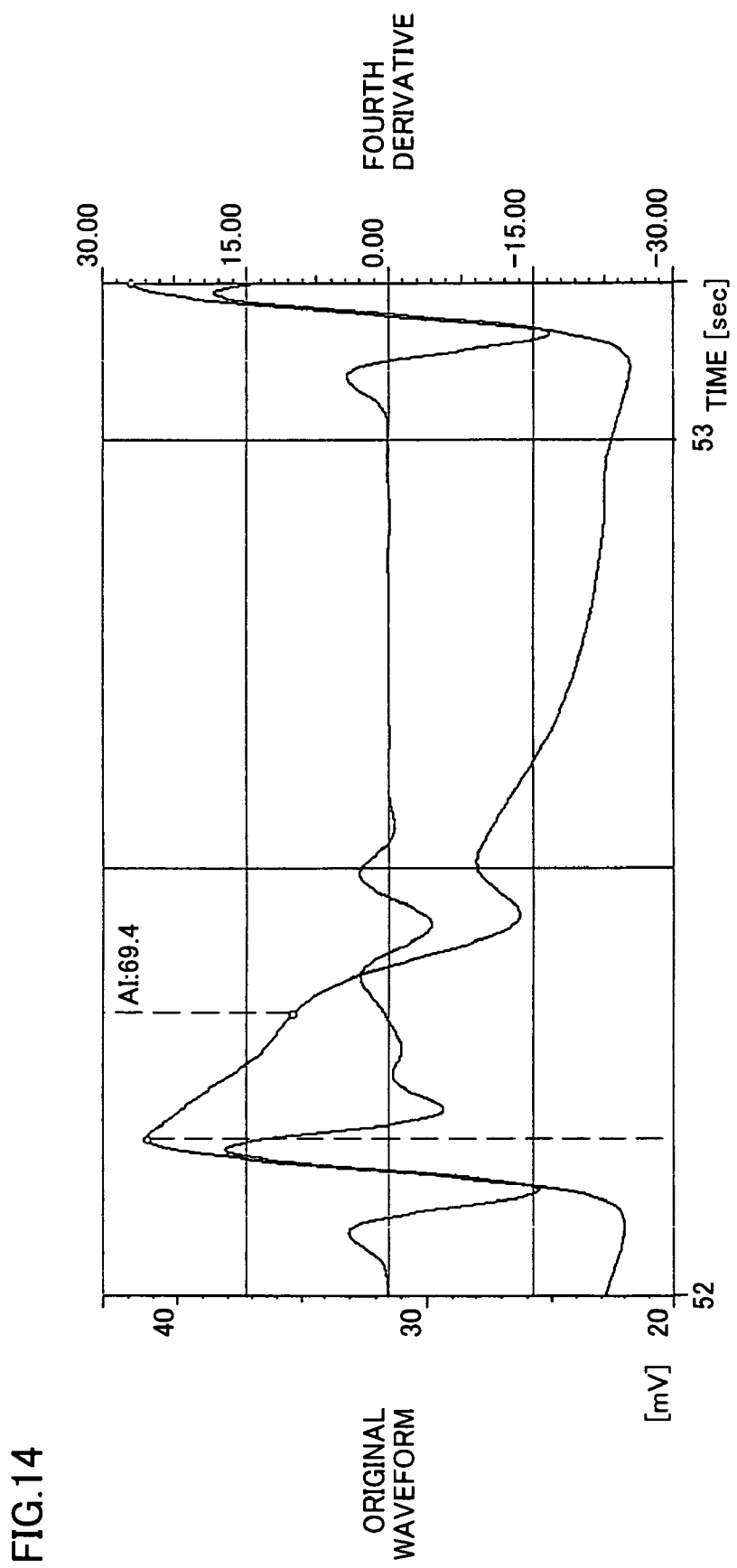
Figure 15:
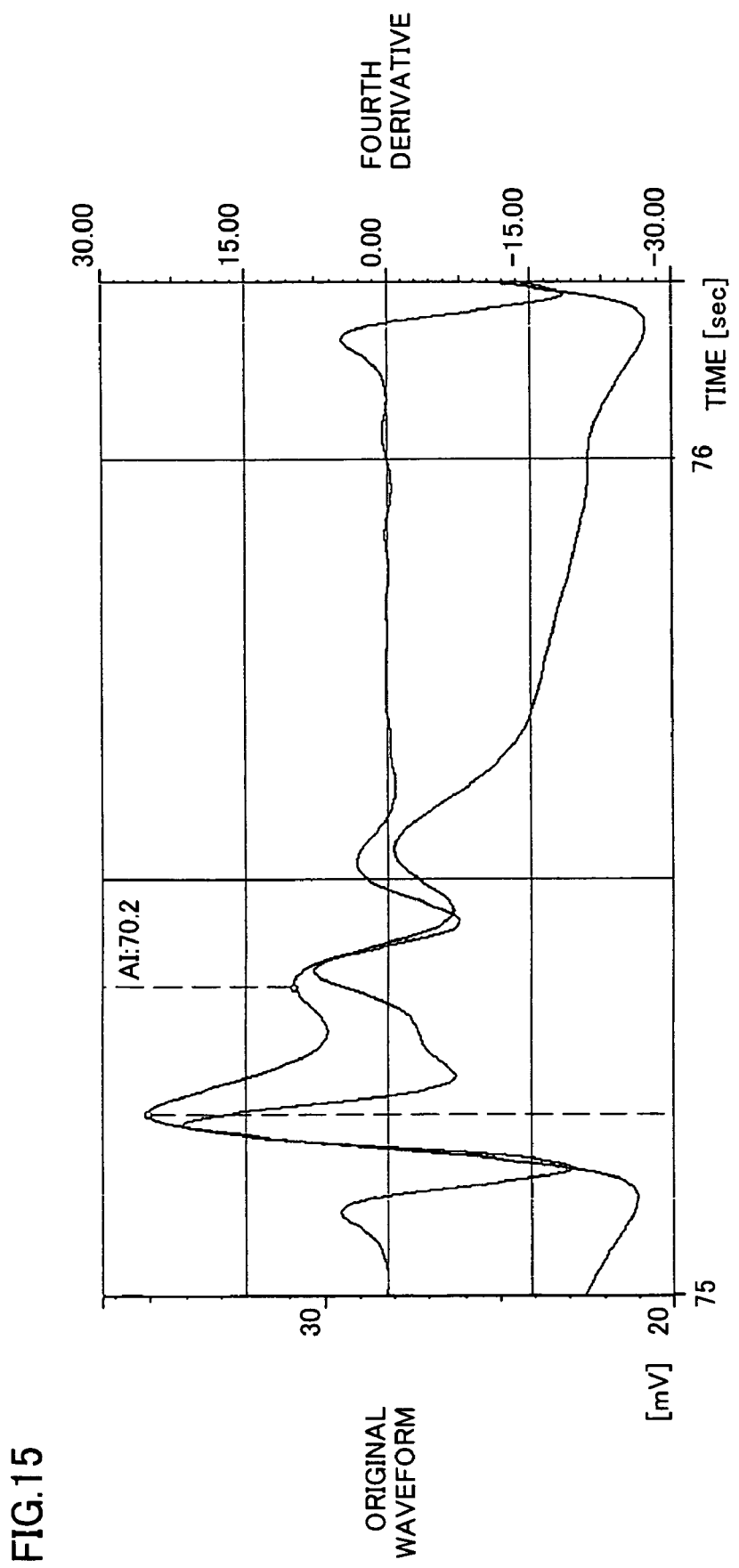
Figure 16:
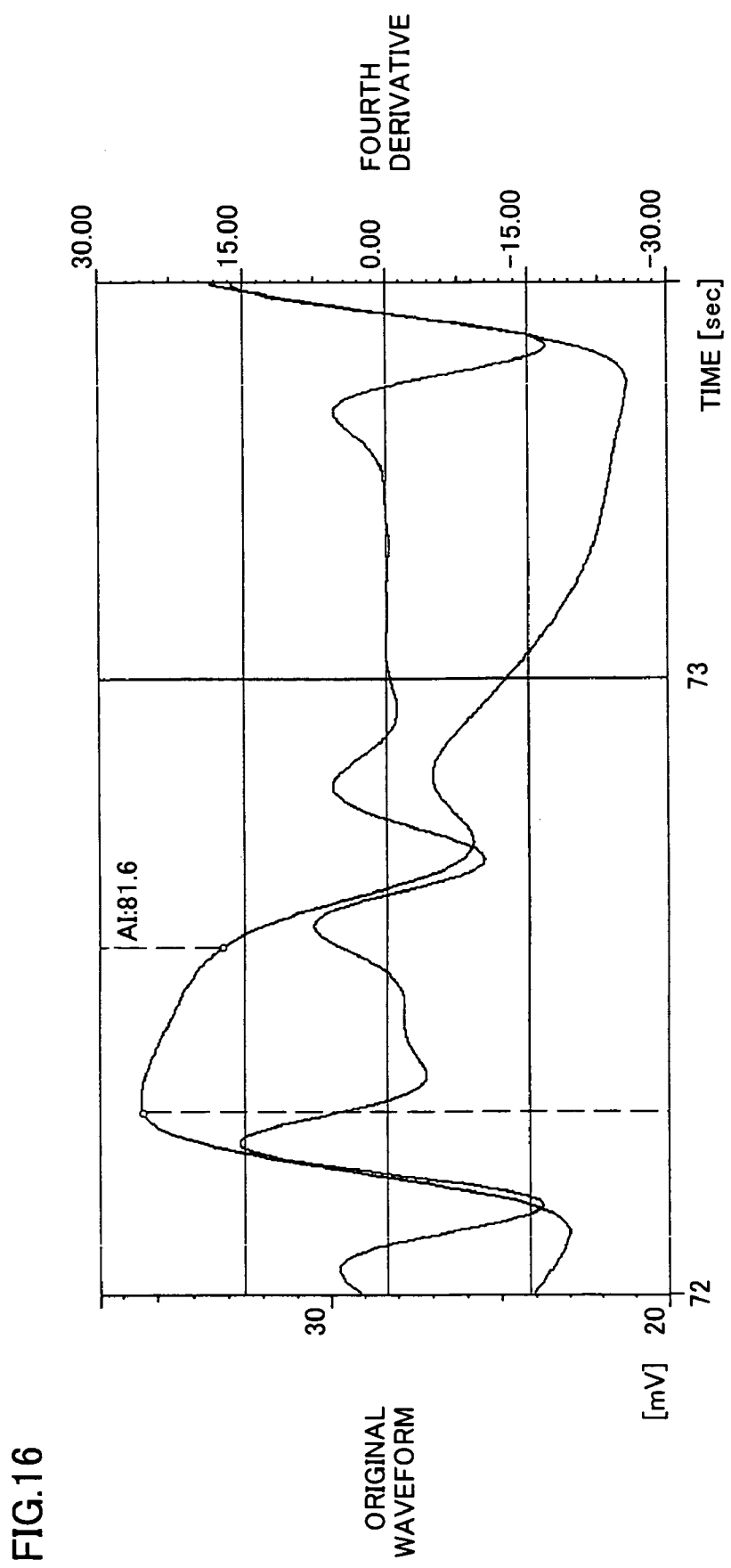
Figure 28:
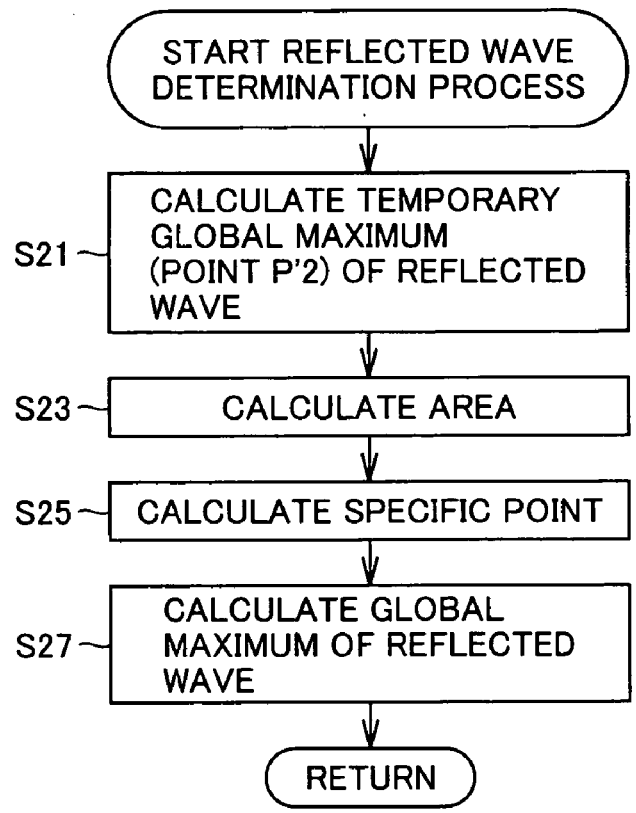
FIG. 28 is a flowchart showing a flow of a reflected wave determination process in step S309' of FIG. 26.

FIG. 28 is a flowchart showing a flow of the process of determining the reflected wave in step S309' of FIG. 26. In the first embodiment, the local maximum of the fourth derivative wave that is present in the section of the descending limb is used to calculate the global maximum of the reflected wave. In the second embodiment, based on the local maximum of the fourth derivative, the correction as shown in steps S23–S27 is made. FIG. 12 illustrates the reflected-wave correction algorithm.

Referring to FIG. 28, a temporary global maximum of the reflected wave (hereinafter referred to as "point P'2") is calculated (step S21). Here, with reference to FIG. 12, a waveform 121 represents a pulse wave and a waveform 122 represents a fourth derivative wave of waveform 121. Point P'2 is a local maximum of fourth derivative wave 122 by which the global maximum of the reflected wave is determined in the first embodiment.

Using the expression indicated below, an area of the fourth derivative wave is calculated (S23). The global minimum of fourth derivative wave 122 between point P'1 and point P'2 is indicated as point P2S. The global minimum of fourth derivative wave 122 between point P'2 and the subsequent local maximum of point APG-E is indicated as point P2E.

After the area between point P2S and point P2E is determined, a point on fourth derivative wave 122 is determined as a specific point in such a manner that the vertical line containing the point divides the area under wave 122 in a predetermined ratio (step S25). The position of the specific point is calculated as the position of the global maximum of the reflected wave (point P2) (step S27).

The operation in step S23 is specifically described. Referring to FIG. 12, respective times (values on the time axis) of point P2S, point P2E, point P'2 and point P2 are indicated respectively as tP2S, tP2E, tP'2 and tP2. Then, the area from point P2S to point P2E is determined by the following expression (5). Here, the amplitude of the fourth derivative at each point is represented as f(t).

$$S = \int_{tP2S}^{tP2E} [f(t) - \text{MAX}\{f(tP2S), f(tP2E)\}] dt \quad (5)$$

MAX {A, B} means that the larger one of A and B is selected.

The operation in step S25 is specifically described. The term $\alpha_2$ in the following expression (6) is a correction coefficient determined in advance and represented as $\{\alpha_2|0 \leq \alpha_2 \leq 1\}$. Such correction coefficient $\alpha_2$ is determined from a comparison between the simulation and the conventional algorithm. The correction coefficient thus determined is for example 0.4 ($\alpha_2$=0.4).

In step S25, based on the area determined by expression (5) above, tP2 satisfying expression (6) below is calculated.

$$\alpha_2 S = \int_{tP2S}^{tP2} [f(t) - \text{MAX}\{f(tP2S), f(tP2E)\}] dt \quad (6)$$

In step S27, the position of point tP2 determined by expression (6) is determined as the position of the global maximum of the reflected wave.

In the second embodiment, CPU 11 calculates AI for example based on the global maxima of the ejected wave and the reflected wave calculated by the correction expressions described above.

FIGS. 13 to 16 each show an example of measuring AI from a pulse wave of a living body in the second embodiment.

As discussed above, in the second embodiment, the global maxima of the ejected wave and the reflected wave that are characteristic points of the pulse wave are determined by using the correction expressions appropriate for actual situations, and thus the pulse wave can more accurately be analyzed.

Third Embodiment

In a third embodiment of the present invention, a pulse wave analysis apparatus is similar in configuration and basic operation to those of the first embodiment and the second embodiment.

In the first and second embodiments, AI is determined as an index (characteristic value) of the pulse wave analysis.

However, the reflected wave is superimposed on the ejected wave as the ejected wave attenuates, and therefore, as the time consumed by the reflection to return is longer, AI tends to be larger. In other words, the magnitude of AI is determined by the magnitude of the reflected wave and the arrival time of the reflected wave.

Therefore, even for the same magnitude of AI, factors determining this AI could be different. For example, it is considered that the arrival time of the reflected wave is associated with the point of reflection and the pulse wave propagation velocity and varies depending on illness.

Accordingly, in order to provide to a subject for example highly precise results of determination of AI, it would be effective to analyze the time component and the amplitude component separately.

Then, the pulse wave analysis apparatus of the third embodiment calculates the index described below as an index used for more effectively analyzing AI. Specifically, in the third embodiment, in addition to AI, other characteristic values are calculated in step S219 of FIG. 2. In the third embodiment, it is supposed that the method of calculating a characteristic point described in connection with the first embodiment is used to calculate the global maximum of the ejected wave and the global maximum of the reflected wave. In the third embodiment as well, the process similar to that shown in the flowchart of FIG. 7 is performed to calculate characteristic values described below in step S311.

Figure 17:
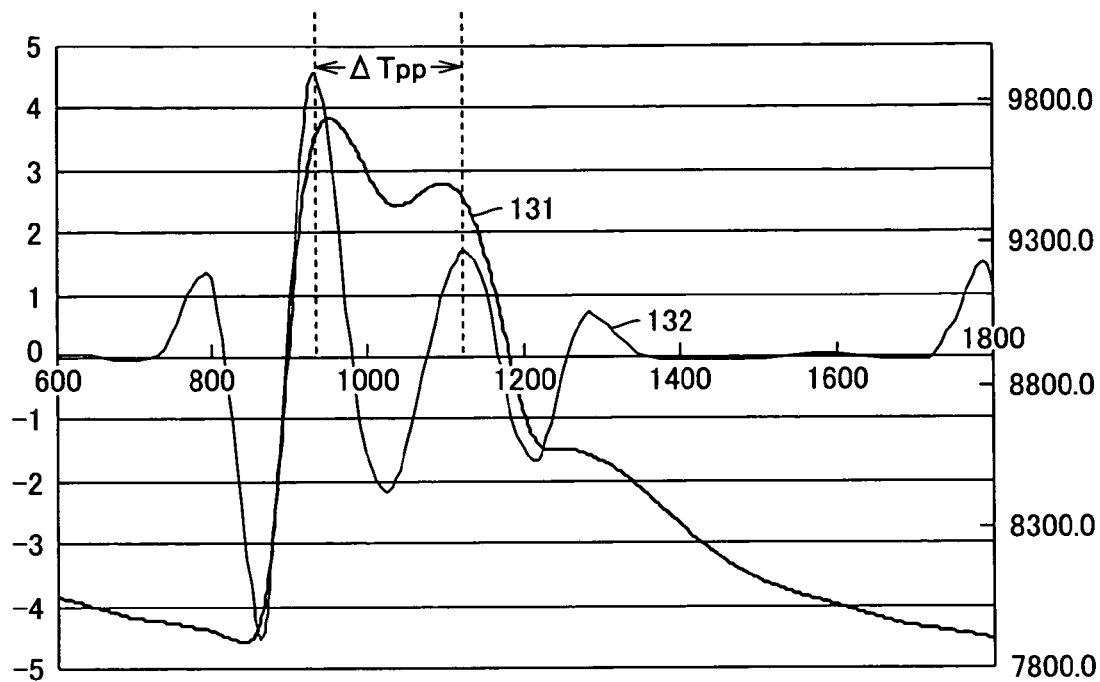
FIG. 17 shows a specific example of calculation of ΔTpp.
Figure 18:
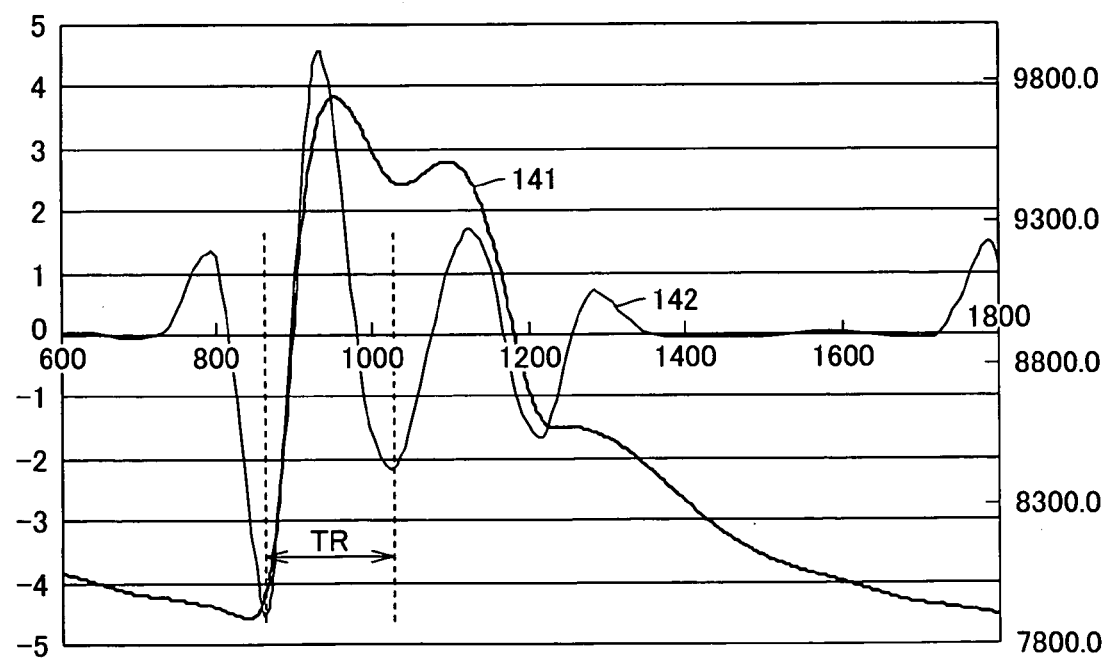
FIG. 18 shows a specific example of calculation of TR.

As an index for analyzing the time component, "ΔTpp" or "TR (Traveling time to Reflected wave)" can be used. ΔTpp and TR are known indices. FIG. 17 shows ΔTpp and FIG. 18 shows TR. A pulse wave 131 shown in FIG. 17 and a pulse wave 141 shown in FIG. 18 are identical to pulse wave 81 in FIG. 8 with which AI is determined in the first embodiment. Further, a waveform 132 shown in FIG. 17 and a waveform 142 shown in FIG. 18 respectively represent fourth derivative waves derived from pulse wave 131 and pulse wave 141.

Referring to FIG. 17, ΔTpp is an index representing a time interval between the global maximum of the ejected wave and the global maximum of the reflected wave. In the third embodiment, this index is determined by the expression ΔTpp=(value of coordinate on time axis of global maximum of reflected wave)−(value of coordinate on time axis of global maximum of ejected wave). In FIG. 17, the determined index is 200 ms (ΔTpp=200 ms). Accordingly, it is seen that, regarding the pulse wave with its AI calculated as 80% (AI=80%) by the pulse wave analysis apparatus of the first embodiment, the time difference between respective global maxima of the ejected wave and the reflected wave is 200 ms.

Referring to FIG. 18, TR is an index representing a time interval between the rising point of the ejected wave and the rising point of the reflected wave. In the third embodiment, the rising point of the ejected wave and the rising point of the reflected wave are determined by local minima of fourth derivative wave 142. Accordingly, in order to calculate TR, the rising point of the ejected wave is calculated in the ejected wave determination step (step S307) of FIG. 7 and the rising point of the reflected wave is calculated in the reflected wave determination step (step S309) of FIG. 7.

With reference to FIG. 18, in the third embodiment, among local minima of fourth derivative wave 142 that are detected in the section of the ascending limb from the pulse wave starting point to the global maximum of pulse wave 141, the minimum one is calculated as the rising point of the ejected wave. Further, among local minima of fourth derivative wave 142 that are detected in the section of the descending limb from the global maximum to the dicrotic notch point of pulse wave 141, the minimum one is calculated as the rising point of the reflected wave. The rising points of the ejected wave and the reflected wave thus determined are used to calculate TR.

In the third embodiment, TR is determined by the expression TR=(value of coordinate on time axis of rising point of reflected wave)−(value of coordinate on time axis of rising point of ejected wave). In FIG. 18, the determined index is 180 ms (TR=180 ms). Accordingly, it is seen that, regarding the pulse wave with its AI calculated as 80% (AI=80%) by the pulse wave analysis apparatus of the first embodiment, the time difference between respective rising points of the ejected wave and the reflected wave is 180 ms.

No firm index for analyzing the amplitude component of the reflected wave has been found. Then, a simulation as described below is conducted for finding an index to analyze the amplitude component of the reflected wave.

In connection with FIGS. 20A–20C and FIGS. 21–23, the simulation for analyzing the amplitude component of the reflected wave is described. Here, in FIGS. 20A, 20B, 20C and 22, the abscissa axis indicates time (in seconds) and the ordinate axis indicates relative pressure (without unit).

Process 1

Figure 20A:
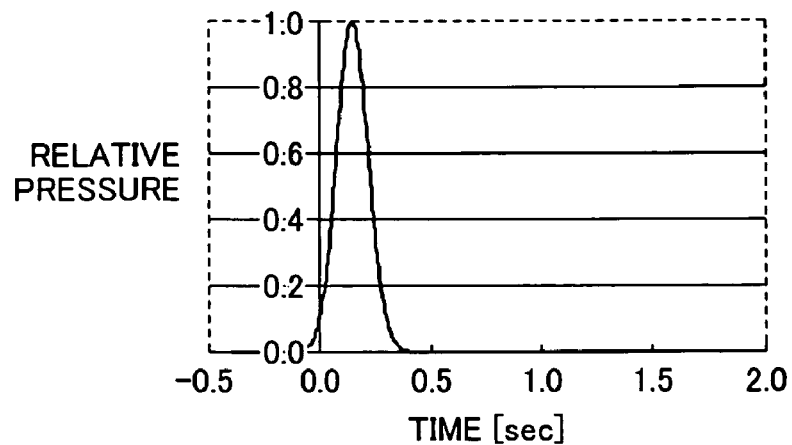
FIGS. 20A–20C each show an exemplary simulation for analyzing an amplitude component of a reflected wave.

Referring to FIG. 20A, a Gaussian function is used to artificially generate an ejected wave of the heart. It is supposed that the amplitude of the waveform is 1. The waveform generated here is regarded as an ejected wave.

Process 2

Figure 20B:
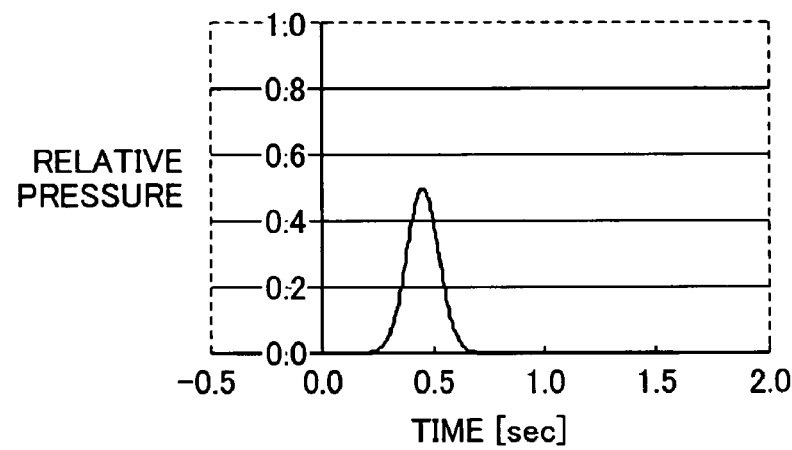

Referring to FIG. 20B, with respect to the ejected wave generated in process 1 described above, a waveform of a certain ratio is generated and the generated waveform is shifted by a certain time. For example, the certain ratio is 50%. The waveform generated here is regarded as a reflected wave.

Process 3

A third waveform is generated as done in process 2.

Process 4

Figure 20C:
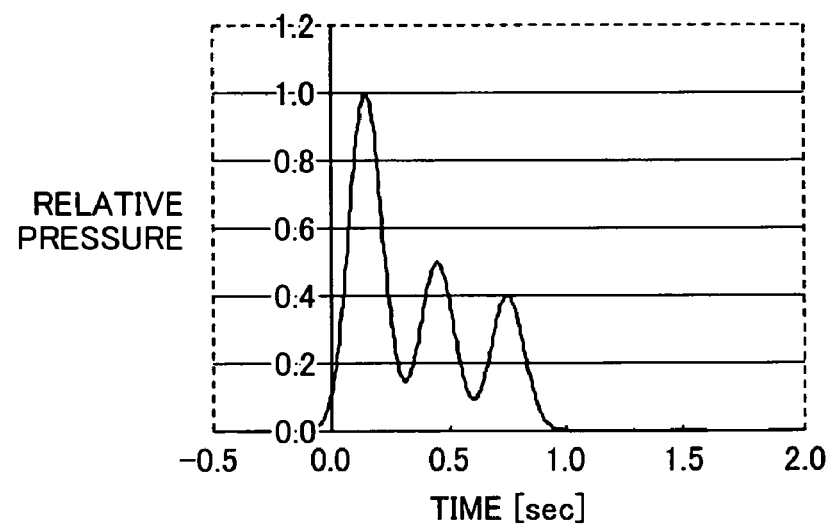

The waveforms generated in processes 1 to 3 respectively are added together to generate the waveform as shown in FIG. 20C.

Process 5

Figure 21:
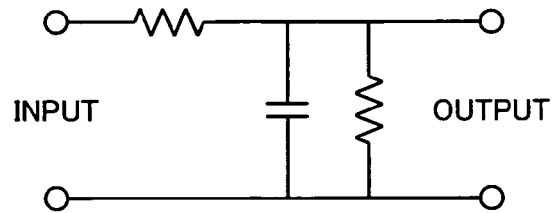
FIG. 21 shows a specific example of a simple Windkessel model used for the simulation shown in FIGS. 20A–20C.
Figure 22:
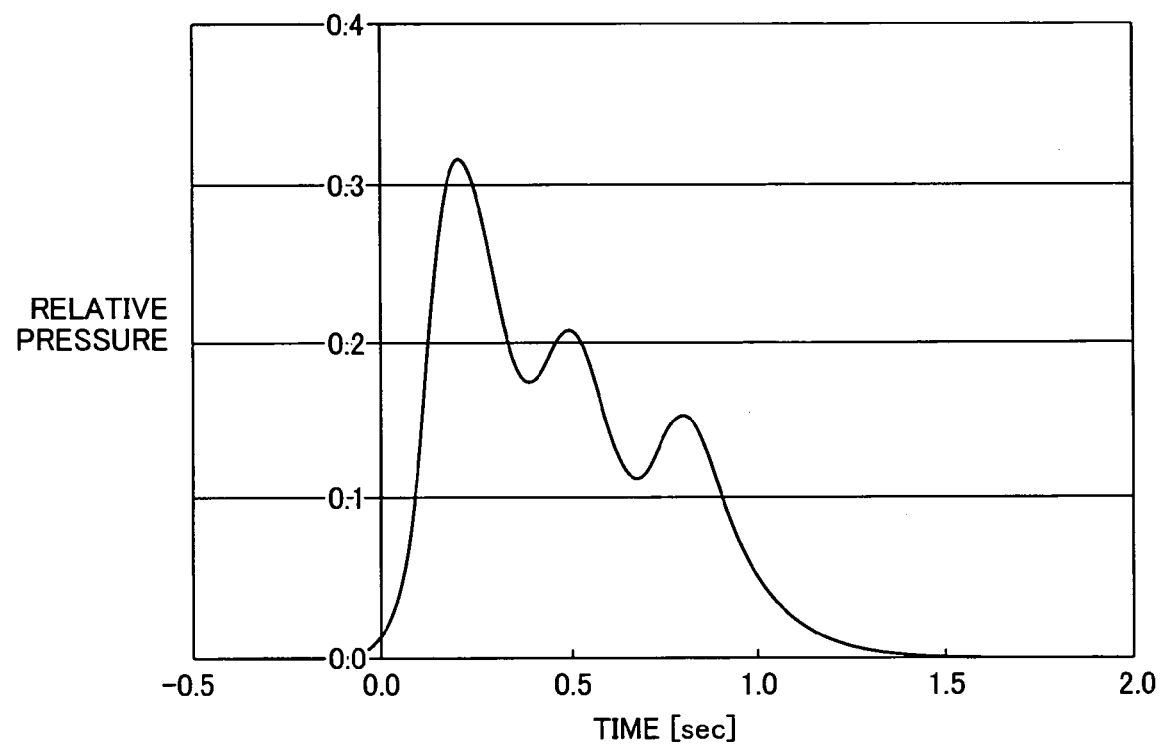
FIG. 22 shows a final waveform obtained by the simulation shown in FIGS. 20A–20C.

In order to cause the same phenomenon as that of an actual blood circulatory system, the waveform generated in process 4 above is input to a simple Windkessel model. Specifically, the simple Windkessel model is the one as shown in FIG. 21. The waveform is input to such a simple Windkessel model and an operation is performed thereon to generate a final waveform as shown in FIG. 22.

Processes 1 to 5 described above are repeated multiple times while the amplitude of the waveform (reflected wave) generated in process 2 is varied. The results of the simulation are shown in FIG. 23.

Figure 23:
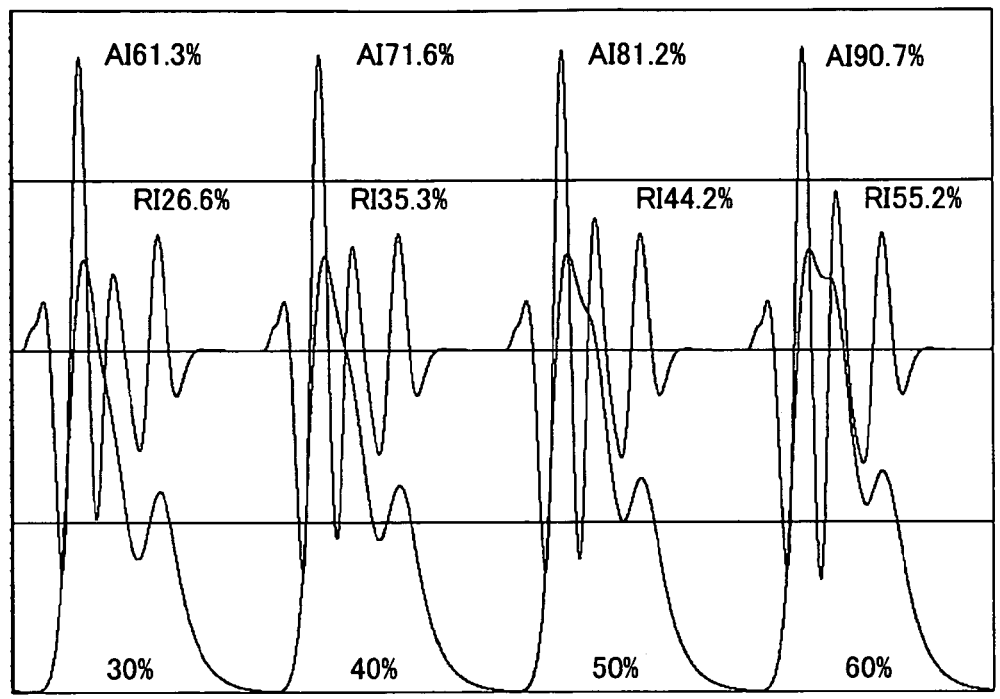
FIG. 23 shows a specific example of the results of the simulation shown in FIGS. 20A–20C, 21 and 22.

FIG. 23 shows exemplary waveforms generated in the simulation by varying the amplitude of the waveform generated in process 2. The ratio of the amplitude of the waveform (hereinafter referred to as "reflected wave amplitude ratio") is 30%, 40%, 50% and 60%.

Using the final waveform generated in process 5 above, AI is calculated by the AI calculation algorism. Referring to FIG. 23, AI for the reflected wave amplitude ratio of 30% is 61.3%, AI for that of 40% is 71.6%, AI for that of 50% is 81.2% and AI for that of 60% is 90.7%.

Figure 24:
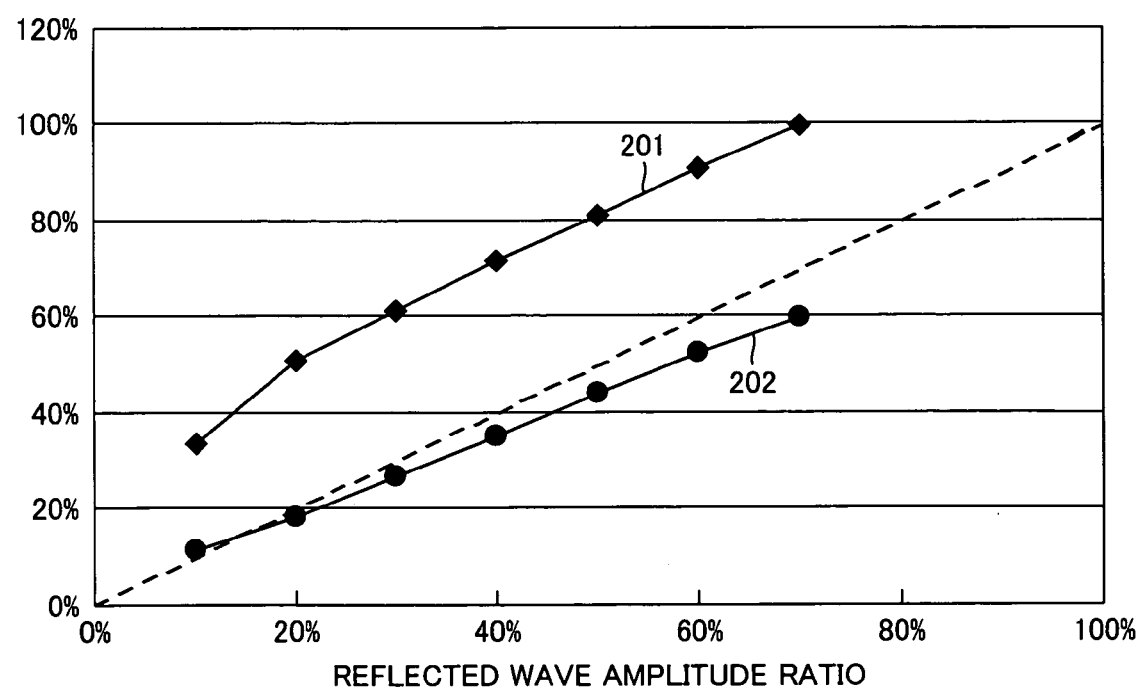
FIG. 24 is a graph showing a comparison of AI and RI each obtained by the simulation with a reflected wave amplitude ratio.

The results of the simulation provide AI as represented by a line 201 of the graph in FIG. 24. In FIG. 24, the abscissa axis indicates the reflected wave amplitude ratio in the simulation. Specifically, the ratio is the value determined by (reflected wave amplitude)/(ejected wave amplitude)×100.

In FIG. 24, the straight broken line represents the ratio of 1:1 between a value on the ordinate axis and a corresponding value on the abscissa axis. From a comparison between points on line 201 and points on the broken line, it is seen that the points on line 201 show different gradients between the section from 10% to 20% and the section larger than 20% and do not linearly change. Thus, AI is determined by any factor except for the reflected wave amplitude ratio.

Accordingly, the actual amplitude of the reflected wave cannot be determined from AI only.

In the same simulation, the local maxima of the fourth derivative wave used in the first embodiment are used to determine the amplitude component of the reflected wave. From the final waveform obtained in process 5 above, local maxima of the fourth derivative are calculated. Among the local maxima of the fourth derivative thus calculated, a local maximum for calculating the global maximum of the ejected wave and a local maximum for calculating the global maximum of the reflected wave are used to determine a characteristic value of the reflected wave amplitude. The characteristic value is hereinafter referred to as "RI (Reflection Index)".

Figure 19:
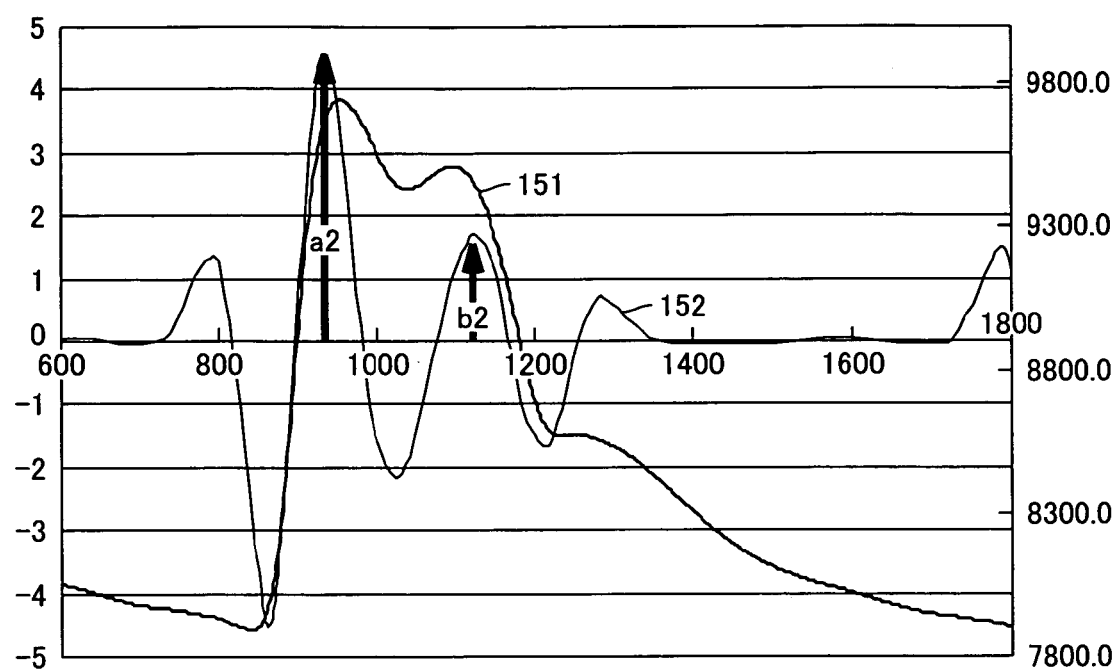
FIG. 19 shows a specific example of calculation of a fourth derivative amplitude ratio (RI).

In connection with FIG. 19, RI is described.

A pulse wave 151 shown in FIG. 19 is identical to pulse wave 81 in FIG. 8 with which AI is determined in the first embodiment. A waveform 152 shown in FIG. 19 is a fourth derivative wave derived from pulse wave 151.

In the third embodiment, RI is calculated by using the local maximum of the fourth derivative wave used for calculating the global maximum of the ejected wave and the local maximum of the fourth derivative wave used for calculating the global maximum of the reflected wave in the first embodiment. With reference to FIG. 19, it is supposed that the local maximum of the fourth derivative wave used for calculating the global maximum of the ejected wave has amplitude a2 and the local maximum of the fourth derivative wave used for calculating the global maximum of the reflected wave has amplitude b2. RI in this case is determined by the expression RI (%)=b2/a2×100. In FIG. 19, the calculated RI is 30 (RI=30%).

Then, the simulation in processes 1 to 5 is used to examine to which degree RI reflects the amplitude component of the reflected wave.

Referring again to FIG. 23, when the reflected wave amplitude ratio is 30%, 40%, 50% and 60% in the simulation, RI is 26.6%, 35.3%, 44.2% and 55.2% respectively.

The results are confirmed with reference to the graph in FIG. 24. A line 202 representing RI is located considerably closer to the position of the broken straight line. It is seen therefrom that RI almost accurately represents the amplitude component of the reflected wave.

Thus, from RI determined in FIG. 19, it is determined that the pulse wave with AI of 80 (AI=80%) has the ratio of 30% of the amplitude of the reflected wave to that of the ejected wave.

In view of the forgoing, it is seen that as an index for analyzing the time component concerning the reflected wave, such an index as ΔTpp and TR can be used and, as an index for analyzing the amplitude component, RI described above can be used. By calculating these indices, more precise AI can be provided to a subject for example.

The pulse wave analysis apparatus of the third embodiment has the function of calculating one of ΔTpp, TR and RI or all thereof by CPU 11.

According to the above description of the third embodiment, the global maximum of the ejected wave and that of the reflected wave are calculated by the method of calculating a characteristic point described in connection with the first embodiment. The third embodiment, however, is not limited to this. For example, the method of calculating a characteristic point described in connection with the second embodiment may be used to calculate the global maxima of the ejected wave and the reflected wave respectively.

According to the descriptions of the first to third embodiments, the pulse wave is detected by examining changes in pulse pressure by the pressure sensor. The method of detecting the pulse wave, however, is not limited to the above-described one. For example, changes in volume may be examined to detect the pulse wave.

Further, the method of analyzing the pulse waveform of the present invention is not limited to the pulse waveform analysis. For example, the analysis method of the present invention is applicable to any analysis of a different biological wave that is a synthetic wave of a first waveform and a second waveform. The above-described method of analyzing the pulse wave performed by the pulse wave analysis apparatus may be provided in the form of a program. Such a program may be provided as a program product by being recorded on such a computer-readable recording medium as CD-ROM (Compact Disc-ROM), ROM, RAM and memory card. Alternatively, the program may be provided by being recorded on such a recording medium as hard disk included in a computer. Moreover, the program may be provided by being downloaded via a network.

The program product thus provided is executed by being installed in such a program storage unit as hard disk. The program product includes a program itself and a recording medium with the program recorded thereon.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pulse wave analysis apparatus comprising:
a pressure sensor for detecting a pulse wave;
a digital conversion unit for converting a pressure signal from said pressure sensor into a digital signal;
a fourth derivative filter having an adjustable frequency characteristic for obtaining a fourth derivative wave of an original waveform based on said digital signal generated by the conversion by said digital conversion unit;
a local extremum calculation unit for calculating local extrema of said fourth derivative wave in a section of the pulse wave corresponding to one beat; and
a characteristic point calculation unit for calculating a characteristic point of said pulse wave, wherein
said characteristic point calculation unit includes:
a first calculation unit for calculating an early systolic component based on said local extrema of said fourth derivative wave; and
a second calculation unit for calculating a late systolic component based on said local extrema of said fourth derivative wave.

2. The pulse wave analysis apparatus according to claim 1, wherein
said first calculation unit includes a first characteristic point calculation unit for calculating a first characteristic point corresponding to a global maximum of said early systolic component by using a local maximum that is one of said local extrema of said fourth derivative wave and is located on an ascending limb from a pulse wave starting point to a pulse wave global-maximum point.

3. The pulse wave analysis apparatus according to claim 2, wherein
said first calculation unit further includes a global maximum calculation unit for calculating the global maximum of said early systolic component based on a positional relation between said pulse wave starting point, said calculated first characteristic point and said pulse wave global-maximum point.

4. The pulse wave analysis apparatus according to claim 2, wherein
said second calculation unit includes:
a second characteristic point calculation unit for calculating a second characteristic point corresponding to a global maximum of said late systolic component by using a local maximum that is one of said local extrema of said fourth derivative wave and is located in a section of a descending limb from said pulse wave global-maximum point to a pulse-wave dicrotic notch point;
an area calculation unit for calculating an area enclosed by a base and a portion of said fourth derivative wave from a first local minimum to a second local minimum, said first local minimum is one of said local extrema of said fourth derivative wave that is minimum in a section from said calculated first characteristic point to said calculated second characteristic point, said second local minimum is one of said local extrema of said fourth derivative wave that is minimum in a section from said second characteristic point to said pulse-wave dicrotic notch point, and said base is at larger one of said first local minimum and said second local minimum;
a specific point calculation unit for calculating a specific point, on said fourth derivative wave, at which said area calculated by said area calculation unit is divided in a predetermined area ratio; and
a global maximum calculation unit for calculating the global maximum of said late systolic component by using said specific point calculated by said specific point calculation unit.

5. The pulse wave analysis apparatus according to claim 2, wherein
said first calculation unit further includes a rising point calculation unit for calculating a rising point of said early systolic component by using a local minimum that is one of said local extrema of said fourth derivative wave and is minimum in a section from said pulse wave starting point to said calculated first characteristic point.

6. The pulse wave analysis apparatus according to claim 2, wherein
said second calculation unit includes:
a second characteristic point calculation unit for calculating a second characteristic point corresponding to a global maximum of said late systolic component by using a local maximum that is one of said local extrema of said fourth derivative wave and is located in a section of a descending limb from said pulse wave global-maximum point to a pulse-wave dicrotic notch point; and
a rising point calculation unit for calculating a rising point of said late systolic component by using a local minimum that is one of said local extrema of said fourth derivative wave and is minimum in a section from said calculated first characteristic point to said calculated second characteristic point.

7. The pulse wave analysis apparatus according to claim 1, wherein
said second calculation unit includes a second characteristic point calculation unit for calculating a second characteristic point corresponding to a global maximum of said late systolic component by using a local maximum that is one of said local extrema of said fourth derivative wave and is located in a section of a descending limb from a pulse wave global-maximum point to a pulse-wave dicrotic notch point.

8. The pulse wave analysis apparatus according to claim 1, further comprising a unit for calculating a ratio between an amplitude difference between a pulse wave starting point and a point on said pulse wave corresponding to a global maximum of said early systolic component calculated by said first calculation unit and an amplitude difference between said pulse wave starting point and a point on said pulse wave corresponding to a global maximum of said late systolic component calculated by said second calculation unit.

9. The pulse wave analysis apparatus according to claim 1, further comprising a unit for calculating a ratio between an amplitude of a point on said fourth derivative wave used for calculating a global maximum of said early systolic component by said first calculation unit and an amplitude of a point on said fourth derivative wave used for calculating a global maximum of said late systolic component by said second calculation unit.

10. The pulse wave analysis apparatus according to claim 1, further comprising a unit for calculating a time difference between a global maximum of said early systolic component calculated by said first calculation unit and a global maximum of said late systolic component calculated by said second calculation unit.

11. The pulse wave analysis apparatus according to claim 1, further comprising a unit for calculating a time difference between a rising point of said early systolic component calculated by said first calculation unit and a rising point of said late systolic component calculated by said second calculation unit.

12. A pulse wave analysis program product on a computer readable medium for a computer to execute an analysis program of a pulse wave that is a composite wave of a first waveform and a second waveform, said analysis program comprising:
an obtaining step for obtaining a fourth derivative wave from the pulse wave corresponding to one beat;
an extracting step for extracting local extrema of said obtained fourth derivative wave;
a first calculation step for calculating said first waveform based on said extracted local extrema; and
a second calculation step for calculating said second waveform based on said extracted local extrema.

13. The pulse wave analysis program product according to claim 12, wherein
said first calculation step includes the step of calculating a first characteristic point corresponding to a global maximum of said first waveform by using a local maximum that is one of said extracted local extrema and is located on an ascending limb from a pulse wave starting point to a pulse wave global-maximum point.

14. The pulse wave analysis program product according to claim 13, wherein
said first calculation step further includes the step of calculating the global maximum of said first waveform based on a positional relation between said pulse wave starting point, said calculated first characteristic point and said pulse wave global-maximum point.

15. The pulse wave analysis program product according to claim 13, wherein
said second calculation step includes the steps of:
calculating a second characteristic point corresponding to a global maximum of said second waveform by using a local maximum that is one of said extracted local extrema and is located in a section of a descending limb from said pulse wave global-maximum point to a pulse-wave dicrotic notch point;
calculating an area enclosed by a base and a portion of said fourth derivative wave from a first local minimum to a second local minimum, said first local minimum is one of said extracted local extrema that is minimum in a section from said calculated first characteristic point to said calculated second characteristic point, said second local minimum is one of said extracted local extrema that is minimum in a section from said second characteristic point to said pulse-wave dicrotic notch point, and said base is at larger one of said first local minimum and said second local minimum;
calculating a specific point, on said fourth derivative wave, at which an area has a predetermined area ratio relative to said calculated area; and
calculating the global maximum of said second waveform by using said calculated specific point.

16. The pulse wave analysis program product according to claim 13, wherein
said first calculation step further includes the step of calculating a rising point of said first waveform by using a local minimum that is one of said extracted local extrema and is minimum in a section from said pulse wave starting point to said calculated first characteristic point.

17. The pulse wave analysis program product according to claim 13, wherein
said second calculation step includes the steps of:
calculating a second characteristic point corresponding to a global maximum of said second waveform by using a local maximum that is one of said extracted local extrema and is located in a section of a descending limb from said pulse wave global-maximum point to a pulse-wave dicrotic notch point; and
calculating a rising point of said second waveform by using a local minimum that is one of said extracted local extrema and is minimum in a section from said calculated first characteristic point to said calculated second characteristic point.

18. The pulse wave analysis program product according to claim 12, wherein
said second calculation step includes the step of calculating a second characteristic point corresponding to a global maximum of said second waveform by using a local maximum that is one of said extracted local extrema and is located in a section of a descending limb from a pulse wave global-maximum point to a pulse-wave dicrotic notch point.

19. The pulse wave analysis program product according to claim 12, wherein
said analysis program further comprises the step of calculating a ratio between an amplitude difference between a pulse wave starting point and a point on said pulse wave corresponding to a global maximum of said first waveform calculated in said first calculation step and an amplitude difference between said pulse wave starting point and a point on said pulse wave corresponding to a global maximum of said second waveform calculated in said second calculation step.

20. The pulse wave analysis program product according to claim 12, wherein
said analysis program further comprises the step of calculating a ratio between an amplitude of a point on said fourth derivative wave used for calculating a global maximum of said first waveform in said first calculation step and an amplitude of a point on said fourth derivative wave used for calculating a global maximum of said second waveform in said second calculation step.

21. The pulse wave analysis program product according to claim 12, wherein
said analysis program further comprises the step of calculating a time difference between a global maximum of said first waveform calculated in said first calculation step and a global maximum of said second waveform calculated in said second calculation step.

22. The pulse wave analysis program product according to claim 12, wherein
said analysis program further comprises the step of calculating a time difference between a rising point of said first waveform calculated in said first calculation step and a rising point of said second waveform calculated in said second calculation step.

* * * * *